(12) United States Patent
Luly et al.

(10) Patent No.: US 9,718,851 B2
(45) Date of Patent: Aug. 1, 2017

(54) DEUTERATED NUCLEOSIDE/TIDE DERIVATIVES

(71) Applicant: Enanta Pharmaceuticals, Inc., Watertown, MA (US)

(72) Inventors: Jay R. Luly, Wellesley, MA (US); Bin Wang, Brigton, MA (US); Guoqiang Wang, Belmont, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 14/933,752

(22) Filed: Nov. 5, 2015

(65) Prior Publication Data

US 2016/0130294 A1   May 12, 2016

Related U.S. Application Data

(60) Provisional application No. 62/076,097, filed on Nov. 6, 2014.

(51) Int. Cl.
| | |
|---|---|
| *A01N 43/04* | (2006.01) |
| *A61K 31/70* | (2006.01) |
| *C07H 19/10* | (2006.01) |
| *A61K 31/7072* | (2006.01) |
| *A61K 45/06* | (2006.01) |
| *C07H 19/06* | (2006.01) |
| *A61K 31/706* | (2006.01) |
| *A61K 31/7064* | (2006.01) |
| *A61K 31/7068* | (2006.01) |

(52) U.S. Cl.
CPC ......... *C07H 19/10* (2013.01); *A61K 31/7072* (2013.01); *A61K 45/06* (2013.01); *C07H 19/06* (2013.01); *A61K 31/706* (2013.01); *A61K 31/7064* (2013.01); *A61K 31/7068* (2013.01)

(58) Field of Classification Search
None
See application file for complete search history.

(56) References Cited

U.S. PATENT DOCUMENTS

| | | | |
|---|---|---|---|
| 5,721,350 | A | 2/1998 | Chattopadhyaya |
| 5,750,806 | A | 5/1998 | Brocker et al. |
| 6,812,219 | B2 | 11/2004 | LaColla et al. |
| 6,914,054 | B2 | 7/2005 | Sommadossi et al. |
| 7,247,621 | B2 | 7/2007 | Hong et al. |
| 7,438,920 | B1 | 10/2008 | Kim et al. |
| 7,589,077 | B2 | 9/2009 | Kumar et al. |
| 7,608,600 | B2 | 10/2009 | Storer et al. |
| 7,625,875 | B2 | 12/2009 | Gosselin et al. |
| 7,951,787 | B2 | 5/2011 | McGuigan |
| 8,163,707 | B2 | 4/2012 | Qiu et al. |
| 8,399,429 | B2 * | 3/2013 | Jonckers ............ C07H 19/10 514/43 |
| 8,637,475 | B1 | 1/2014 | Storer et al. |
| 2003/0087873 | A1 | 5/2003 | Stuyver et al. |
| 2004/0006007 | A1 | 1/2004 | Gosselin et al. |
| 2005/0009737 | A1 | 1/2005 | Clark et al. |
| 2007/0015905 | A1 | 1/2007 | LaColla et al. |
| 2008/0139802 | A1 | 6/2008 | Axt et al. |
| 2009/0306007 | A1 | 12/2009 | Wagner |
| 2009/0317361 | A1 | 12/2009 | Cho et al. |
| 2010/0016251 | A1 | 1/2010 | Sofia et al. |
| 2010/0074889 | A1 | 3/2010 | Qiu et al. |

(Continued)

FOREIGN PATENT DOCUMENTS

| | | |
|---|---|---|
| WO | 0132153 A2 | 5/2001 |
| WO | 0160315 A2 | 8/2001 |

(Continued)

OTHER PUBLICATIONS

Powdrill et al. Viruses (2010), vol. 2, pp. 2169-2195.*
"Representative." Merriam-Webster.com. Merriam-Webster, n.d. Web. Nov. 18, 2016.*
Chirakul et al. Organic Letters (2003), vol. 5, pp. 917-919.*
Li, et al., Synthesis of 2'-C-Branched Nucleosides, Organic Preparations and Procedures International, 42:191-283 (2010).
Hayashi, et al., "Adenallene and cytallene: Acyclic nucleoside analogues that inhibit replication and cytopathic effect of human immunodeficiency virus in vitro," Proceedings of the National Academy of Science, 85:6127-6131,1988.

(Continued)

*Primary Examiner* — Patrick Lewis
(74) *Attorney, Agent, or Firm* — Edgar W. Harlan; Carolyn S. Elmore, Esq.; Elmore Patent Law Group, P.C.

(57) ABSTRACT

The present invention provides nucleoside phosphoramidate compounds of Formula I,

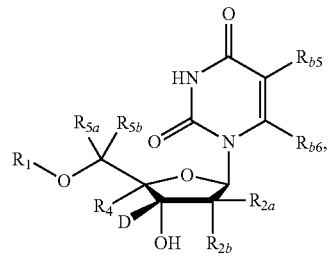

where $R_1$, $R_{2a}$, $R_{2b}$, $R_4$, $R_{5a}$, $R_{5b}$, $R_{b5}$, $R_{b6}$ and D are as defined herein. The invention further includes pharmaceutical compositions comprising a compound of Formula I, methods of use of these compounds for treating a viral infection, and methods of producing these compounds.

12 Claims, No Drawings

(56) References Cited

U.S. PATENT DOCUMENTS

| | | |
|---|---|---|
| 2010/0074890 A1 | 3/2010 | Hagel et al. |
| 2010/0081628 A1 | 4/2010 | Du et al. |
| 2010/0279973 A1 | 11/2010 | Chun et al. |
| 2011/0251152 A1 | 10/2011 | Ross et al. |
| 2011/0257122 A1 | 10/2011 | Sofia et al. |
| 2012/0237480 A1 | 9/2012 | Or et al. |
| 2013/0078217 A1 | 3/2013 | Wang et al. |
| 2013/0315864 A1 | 11/2013 | Or et al. |
| 2014/0039175 A1 | 2/2014 | Srivastava et al. |
| 2014/0219958 A1 | 8/2014 | Luly et al. |
| 2014/0309189 A1 | 10/2014 | Deshpande et al. |

FOREIGN PATENT DOCUMENTS

| | | |
|---|---|---|
| WO | 0190121 A2 | 11/2001 |
| WO | 2004099241 A1 | 11/2004 |
| WO | 2005003147 A2 | 1/2005 |
| WO | 2008045419 A1 | 4/2008 |
| WO | 2010135569 A1 | 11/2010 |
| WO | 2012040127 A1 | 3/2012 |
| WO | 2012094248 | 7/2012 |
| WO | 2013187978 | 12/2013 |
| WO | 2014076490 | 5/2014 |
| WO | 2014169278 | 10/2014 |
| WO | 2014169280 | 10/2014 |

OTHER PUBLICATIONS

International Search Report for PCT/US12/29381, dated Jun. 28, 2012.
Foldesi, et al., "The Synthesis of Deuterionucleosides," Nucleoside, Nucleotides and Nucleic Acids, 19(10-12):1615-1656, 2000.
Sajiki, et al., "Palladium-Catalyzed Base-Selective H-D Exchange Reaction of Nucleosides in Deuterium Oxide," Synlett, 9:1385-1388, 2005.
Maeda, et al., "Chemical Alteration of Nucleic Acids and Their Components. XI1) Hydrogen-Deuterium Exchange of Nucleosides and Nucleotides Catalyzed by Platinum," Tetrabedron Letters, 19:1643-1646. 1975.
Banker, et al., "Modern Pharmaceutics," Marcel Dekker, Inc., 3:596, 1996.
Wolff, et al., "Burger's Medicinal Chemistry and Drug Discovery," John Wiley & Sons, 5(1):975-977, 1995.
Atzrodt, et al., "The Renaissance of H/D/ Exchange," Angew. Chem. Int. Ed., 46:7744-7765, 2007.
Jung, et al., "Preparation of 4'-Substituted Thymidines by Substitution of the Thymidine 5'-Esters," J. Org. Chem., 66:2624-2635. 2001.
Esaki, et al., "Synthesis of Base-Selectively Deuterium-Labelled Nucleosides by the Pd/C-Catalyzed H-D Exchange Reaction in Deuterium Oxide," Heterocycles, 66:361-369, 2005.
De Voss, et al., "General Approach to the Synthesis of Specifically Deuterium-Labeled Nucleosides," J. Org. Chem., 59:2715-2723, 1994.
Chun, et. al., "Synthesis of Stable Isotope Labeled Analogs of the Anti-Hepatitis C Virus Nucleotide Prodrugs PSI-7977 and PSI-352938," Nucleosides, Nucleotides and Nucleic Acids, 30:886, 2011.
Maurel, et al., "Detection of reactive free radicals derived from nucleosides by liquid chromatography coupled to tandem mass spectrometry of DMPO spin trapping adducts," Rapid Communications in Mass Spectrometery, 20(15):2235-2242, 2006.
Kushner, et al., "Pharmacological uses and perspectives of heavy water and deuterated compounds," Canadian Journal of Physiology and Pharmacology, 77(2):79-88, 1999.
Haskins, "the Application of Stable Isotopes in Biomedical Research," Biomedical Mas Spectrometry, 9(7):269-277, 1982.
Pubchem Uridine-5,6-d2, CID 46783218, pp. 1-3, Create Date: Jul. 26, 2010; p. 1; (retrieved on Aug. 25, 2014]. Retrieved from the Internet: <URL:https://pubchem.ncbi.nlm.nih.gov/summary/summary.cgi?cid=46783218>.
U.S. Appl. No. 14/836,157, filed Aug. 26, 2015.
U.S. Appl. No. 14/959,364, filed Dec. 4, 2015.

* cited by examiner

DEUTERATED NUCLEOSIDE/TIDE DERIVATIVES

RELATED APPLICATION

This application claims the benefit of U.S. Provisional Application No. 62/076,097, filed on Nov. 6, 2014. The entire teachings of the above application are incorporated herein by reference.

TECHNICAL FIELD

The present invention relates generally to compounds and pharmaceutical compositions useful as antiviral and anti-proliferative agents. Specifically, the present invention relates to deuterated uridine nucleoside/tide derivatives and methods for their preparation and use.

BACKGROUND OF THE INVENTION

Infection with HCV is a major cause of human liver disease throughout the world. In the US, an estimated 4.5 million Americans are chronically infected with HCV. Although only 30% of acute infections are symptomatic, greater than 85% of infected individuals develop chronic, persistent infection. Treatment costs for HCV infection have been estimated at $5.46 billion for the US in 1997. Worldwide over 200 million people are estimated to be infected chronically. HCV infection is responsible for 40-60% of all chronic liver diseases and 30% of all liver transplants. Chronic HCV infection accounts for 30% of all cirrhosis, end-stage liver disease, and liver cancer in the U.S. The CDC estimates that the number of deaths due to HCV will minimally increase to 38,000/year by the year 2010.

Due to the high degree of variability in the viral surface antigens, existence of multiple viral genotypes, and demonstrated specificity of immunity, the development of a successful vaccine in the near future is unlikely. There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

First identified by molecular cloning in 1989 (Choo, Q-L et al (1989) Science 244:359-362), HCV is now widely accepted as the most common causative agent of post-transfusion non-A, non-B hepatitis (NANBH) (Kuo, G et al (1989) Science 244:362-364). Due to its genome structure and sequence homology, this virus was assigned as a new genus in the Flaviviridae family. Like the other members of the Flaviviridae, such as flaviviruses (e.g. yellow fever virus and Dengue virus types 1-4) and pestiviruses (e.g. bovine viral diarrhea virus, border disease virus, and classic swine fever virus) (Choo, Q-L et al (1989) Science 244:359-362; Miller, R. H. and R. H. Purcell (1990) Proc. Natl. Acad. Sci. USA 87:2057-2061), HCV is an enveloped virus containing a single strand RNA molecule of positive polarity. The HCV genome is approximately 9.6 kilobases (kb) with a long, highly conserved, noncapped 5' nontranslated region (NTR) of approximately 340 bases which functions as an internal ribosome entry site (IRES) (Wang C Y et al.). An RNA pseudoknot is an essential structural element of the internal ribosome entry site located within the hepatitis C virus 5' noncoding region' RNA—A Publication of the RNA Society. 1(5): 526-537, 1995 July). This element is followed by a region which encodes a single long open reading frame (ORF) encoding a polypeptide of ~3000 amino acids comprising both the structural and nonstructural viral proteins.

Upon entry into the cytoplasm of the cell, this RNA is directly translated into a polypeptide of ~3000 amino acids comprising both the structural and nonstructural viral proteins. This large polypeptide is subsequently processed into the individual structural and nonstructural proteins by a combination of host and virally-encoded proteinases (Rice, C. M. (1996) in B. N. Fields, D. M. Knipe and P. M. Howley (eds) Virology $2^{nd}$ Edition, p931-960; Raven Press, N. Y.). There are three structural proteins, C, E1 and E2. The P7 protein is of unknown function and is comprised of a highly variable sequence. There are several non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease. NS5A is a membrane-anchored phosphoprotein that is observed in basally phosphorylated (56 kDa) and hyperphosphorylated (58 kDa) forms. While its function has not fully been elucidated, NS5A is believed to be important in viral replication. The NS5B protein (591 amino acids, 65 kDa) of HCV (Behrens, S. E. et at (1996) *EMBO J.* 151 2-22), encodes an RNA-dependent RNA polymerase (RdRp) activity and contains canonical motifs present in other RNA viral polymerases. The NS5B protein is fairly well conserved both intra-typically (~95-98% amino acid (aa) identity across 1b isolates) and inter-typically (~85% aa identity between genotype 1a and 1b isolates). The essentiality of the HCV NS5B RdRp activity for the generation of infectious progeny virions has been formally proven in chimpanzees (A. A. Kolykhalov et al. (2000) *Journal of Virology*, 74(4): 2046-2051). Thus, inhibition of NS5B RdRp activity (inhibition of RNA replication) is predicted to be useful to treat HCV infection.

Current standard of care (SOD) therapy is the combination of peg-interferon-a and ribavirin. However, this therapy is limited in its clinical effectiveness and only ~50% of genotype 1a patients respond to the therapy. Recent approved NS3 protease inhibitors, Boceprevir and Telaprevir, used in combination with SOC slightly improved effectiveness, but suffered significant side effects, such as rash. Therefore, there is still significant unmet medical need for more effective agents.

Inhibitors of HCV NS5B as potential therapies for HCV infection have been reviewed: S. Tan, A. Pause, Y. Shi, N. Sonenberg, Hepatitis C Therapeutics: Current Status and Emerging Strategies, *Nature Rev. Drug Discov.* 1, 867-881 (2002). The potential for the emergence of resistant HCV strains and the need to identify compounds with Pan-genotypic coverage supports the continuing efforts to identify novel and more effective nucleosides or nucleotides as HCV NS5B polymerase inhibitors.

SUMMARY OF THE INVENTION

In one aspect, the invention provides compounds represented by Formula I, or pharmaceutically acceptable salts, esters, stereoisomer, tautomer, solvate, or combination thereof:

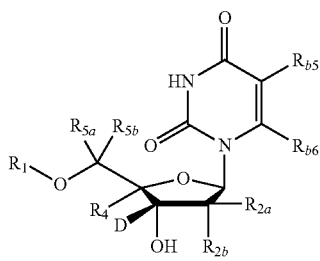

(I)

wherein:

D is deuterium;

$R_1$ is selected from the group consisting of:
1) Hydrogen;
2) $R_6$; wherein $R_6$ is selected from the group consisting of: hydrogen, hydroxy protecting group, —C(O)$R_7$, —C(O)O$R_7$, and —C(O)N$R_{8a}R_{8b}$; wherein $R_7$ is selected from the group consisting of: substituted or unsubstituted —$C_1$-$C_8$ alkyl, substituted or unsubstituted —$C_2$-$C_8$ alkenyl, substituted or unsubstituted —$C_2$-$C_8$ alkynyl, substituted or unsubstituted aryl, substituted or unsubstituted heteroaryl, and substituted or unsubstituted heterocyclic; $R_{8a}$ and $R_{8b}$ are each independently selected from the group consisting of: hydrogen and $R_7$; or alternatively $R_{8a}$ and $R_{8b}$ are taken together with the nitrogen atom to which they are attached form a heterocyclic ring;
3) —P(O)(O$R_{7a}$)(O$R_{7b}$); wherein $R_{7a}$ and $R_{7b}$ are each independently selected from the group consisting of a) hydrogen; and b) unsubstituted or substituted —$C_1$-$C_8$ alkyl;
4) —P(O)(O$R_{7a}$)—O—P(O)(O$R_{7b}$)(O$R_{7c}$); wherein $R_{7a}$ and $R_{7b}$ are previously defined; $R_{7c}$ is selected from the group consisting of a) hydrogen; and b) unsubstituted or substituted —$C_1$-$C_8$ alkyl;
5) —P(O)(O$R_{7a}$)—O—P(O)(O$R_{7b}$)—O—P(O)(O$R_{7c}$)(O$R_{7d}$); wherein $R_{7a}$, $R_{7b}$ and $R_{7c}$ are previously defined; $R_{7d}$ is selected from the group consisting of a) hydrogen; b) unsubstituted or substituted —$C_1$-$C_8$ alkyl; and

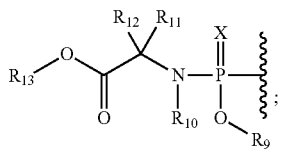

where X is O or S; $R_9$ is $R_7$ wherein $R_7$ is previously defined; $R_{10}$, $R_{11}$ and $R_{12}$ are each independently selected from the group consisting of: a) hydrogen; b) unsubstituted or substituted —$C_1$-$C_8$ alkyl; c) $R_{11}$ is hydrogen, $R_{12}$ and $R_{10}$ are taken together with the intervening carbon and nitrogen atoms to form a heterocyclic ring; d) $R_{11}$ and $R_{12}$ are taken together with the carbon atom to which they are attached to form a ring, such as a carbocyclic or heterocyclic ring; $R_{13}$ is hydrogen or $R_7$, wherein $R_7$ is previously defined;

$R_{2a}$ is selected from the group consisting of:
1) Hydrogen;
2) Deuterium;
3) Halogen;
4) Nitrile;
5) Substituted or unsubstituted —$C_1$-$C_8$ alkyl;
6) Substituted or unsubstituted —$C_2$-$C_8$ alkenyl; and
7) Substituted or unsubstituted —$C_2$-$C_8$ alkynyl;

$R_{2b}$ is selected from the group consisting of:
1) Halogen; and
2) O$R_9$;

$R_9$ at each occurrence is selected from the group consisting of: hydrogen, hydroxy protecting group, $R_{10b}$, —C(O)$R_{10b}$, —C(O)O$R_{10b}$, and —C(O)N$R_{11a}R_{11b}$; wherein $R_{10b}$ at each occurrence is independently selected from the group consisting of: substituted or unsubstituted —$C_1$-$C_8$ alkyl, substituted or unsubstituted —$C_2$-$C_8$ alkenyl, substituted or unsubstituted —$C_2$-$C_8$ alkynyl, substituted or unsubstituted aryl, substituted or unsubstituted heteroaryl, and substituted or unsubstituted heterocyclic; $R_{11a}$ and $R_{11b}$ at each occurrence are each independently selected from the group consisting of:

hydrogen and $R_{10b}$; or alternatively $R_{11a}$ and $R_{11b}$ taken together with the nitrogen atom to which they are attached form a heterocyclic ring;

Or $R_{2a}$ and $R_{2b}$ taken together with the carbon atom to which they are attached to form a 3- to 6-membered cycloalkyl ring or a 3- to 6-membered heterocycloalkyl ring containing one hereroatom selected from N, O, and S, each of which is optionally substituted. In certain embodiments, such a ring can be, but is not limited to, cyclopropyl, oxetane, azetidine;

$R_{5a}$ and $R_{5b}$ are each independently selected from the group consisting of:
1) Hydrogen;
2) Deuterium;
3) Substituted or unsubstituted —$C_1$-$C_8$ alkyl;
4) Substituted or unsubstituted —$C_2$-$C_8$ alkenyl; and
5) Substituted or unsubstituted —$C_2$-$C_8$ alkynyl;
or $R_{5a}$ and $R_{5b}$ are taken together with the carbon atom to which they are attached to form a group selected from —$C_3$-$C_8$ cycloalkyl, —$C_3$-$C_8$ cycloalkenyl, or —$C_3$-$C_8$ cycloalkynyl.

$R_4$ is hydrogen, deuterium, $N_3$, halogen or optionally substituted methyl.

$R_{b5}$ and $R_{b6}$ are each independently selected from the group consisting of:
1) Hydrogen;
2) Deuterium;

In certain embodiments of the compounds of Formula I, $R_{2a}$ is $C_1$-$C_6$-alkyl, preferably methyl or $CD_3$. In certain embodiments of the compounds of Formula I, $R_{2b}$ is hydrogen, halogen, —CN, —$N_3$ or OH, preferably F or OH. In certain embodiments of the compounds of Formula I, $R_4$ is hydrogen, halogen or OH, preferably hydrogen. In certain embodiments of the compounds of Formula I, $R_{5a}$ and $R_{5b}$ are independently hydrogen, deuterium or $C_1$-$C_6$-alkyl or $R_{5a}$ and $R_{5b}$, together with the carbon atom to which they are attached, form a $C_3$-$C_6$-cycloalkyl group. Preferably one of $R_{5a}$ and $R_{5b}$ is methyl and the other is hydrogen or deuterium; $R_{5a}$ and $R_{5b}$ are both deuterium; or $R_{5a}$ and $R_{5b}$, together with the carbon atom to which they are attached, form a cyclopropyl group. In certain embodiments of the compounds of Formula I, $R_9$ is aryl, substituted aryl or $C_1$-$C_6$-alkyl, preferably phenyl, naphthyl, p-fluorophenyl or isopropyl. $R_{11}$ is hydrogen, $C_1$-$C_6$-alkyl or aryl-$C_1$-$C_3$-alkyl, preferably hydrogen, methyl, isopropyl, isobutyl or benzyl. In certain embodiments of the compounds of Formula I, $R_{12}$ is hydrogen. In certain embodiments of the compounds of Formula I, $R_{13}$ is $C_1$-$C_6$-alkyl or aryl-$C_1$-$C_3$-alkyl, preferably hydrogen, methyl, isopropyl, isobutyl or benzyl.

In another embodiment, the present invention provides a pharmaceutical composition comprising a therapeutically effective amount of a compound or combination of compounds of the present invention, or a pharmaceutically acceptable salt form, stereoisomer, tautomer, solvate, or combination thereof, in combination with a pharmaceutically acceptable carrier or excipient.

In yet another embodiment, the present invention provides a method of inhibiting the replication of an RNA or DNA containing virus comprising contacting said virus with a therapeutically effective amount of a compound or a combination of compounds of the present invention, or a pharmaceutically acceptable salt, stereoisomer, tautomer, solvate, or combination thereof. Particularly, this invention is directed to methods of inhibiting the replication of HCV, HBV and/or HIV.

In still another embodiment, the present invention provides a method of treating or preventing infection caused by an RNA or DNA-containing virus comprising administering to a patient in need of such treatment a therapeutically effective amount of a compound or combination of compounds of the present invention, or a pharmaceutically acceptable salt form, stereoisomer, or tautomer, solvate, or combination thereof. Particularly, this invention is directed to methods of treating or preventing infection caused by HCV, HBV and/or HIV.

Yet another embodiment of the present invention provides the use of a compound or combination of compounds of the present invention, or a therapeutically acceptable salt form, stereoisomer or tautomer, solvate, or combination thereof, as defined hereinafter, in the preparation of a medicament for the treatment or prevention of infection caused by RNA or DNA-containing virus, specifically HCV, HBV and/or HIV.

DETAILED DESCRIPTION OF THE INVENTION

A first embodiment of the invention is a compound represented by Formula I as described above, or a pharmaceutically acceptable salt, ester or prodrug thereof.

A second embodiment of the invention is a compound represented by Formula II,

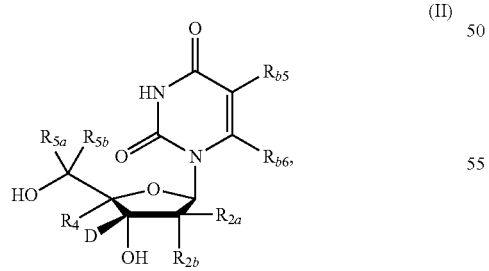

(II)

or a pharmaceutically acceptable salt, ester or prodrug thereof, wherein, $R_{2a}$, $R_{2b}$, $R_4$, $R_{b5}$, $R_{b6}$, $R_{5a}$ and $R_{5b}$ are as previously defined.

Illustrative structures of formula (II) include, but are not limited to, those represented by formulas (II-1~II-24), where $R_{b5}$ and $R_{b6}$ are as previously defined:

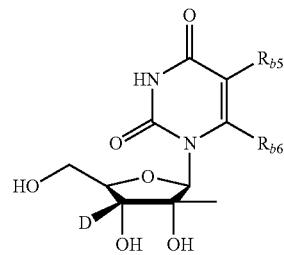
(II-1)

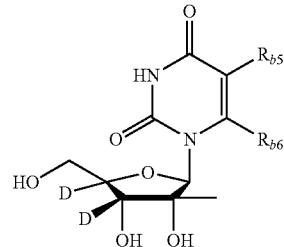
(II-2)

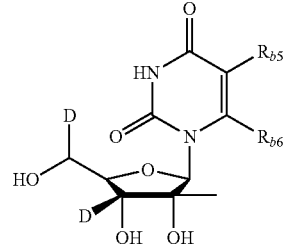
(II-3)

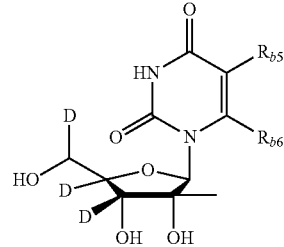
(II-4)

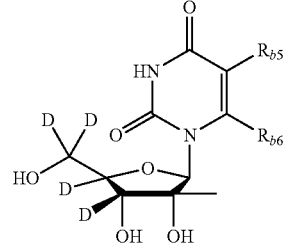
(II-5)

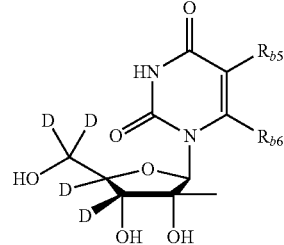
(II-6)

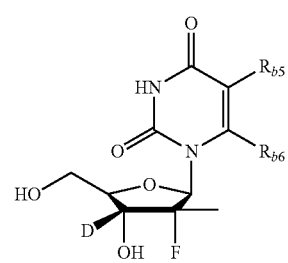
(II-7)
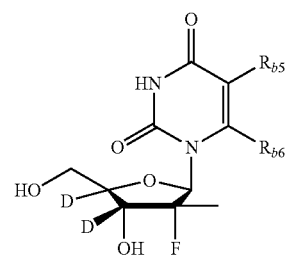
(II-8)
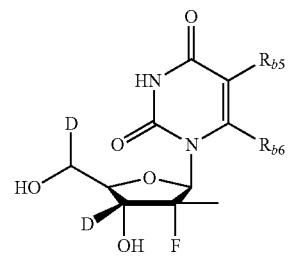
(II-9)
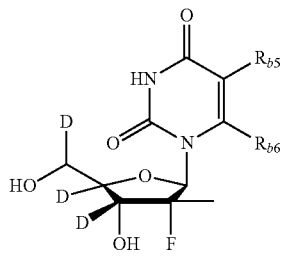
(II-10)
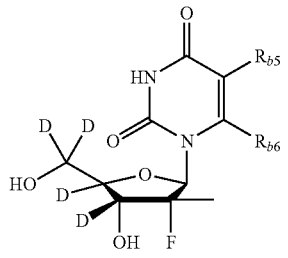
(II-11)
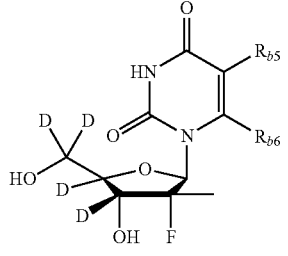
(II-12)
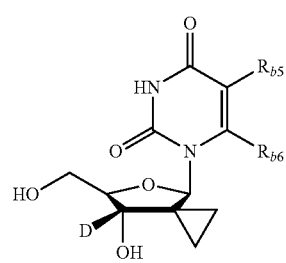
(II-13)
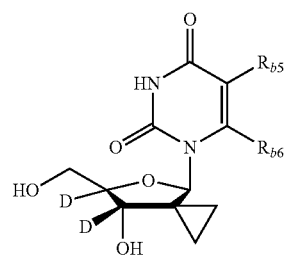
(II-14)
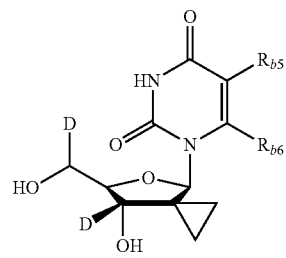
(II-15)
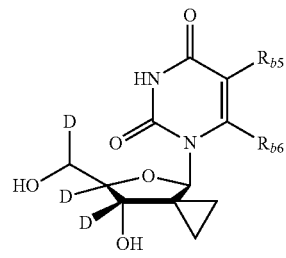
(II-16)
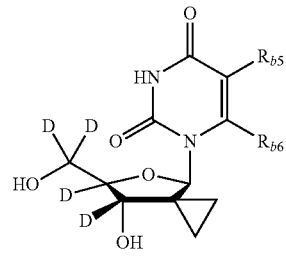
(II-17)
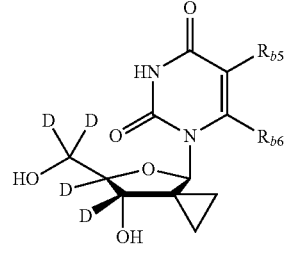
(II-18)

-continued (II-19)
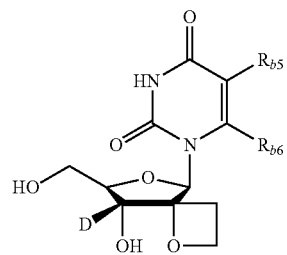

(II-20)
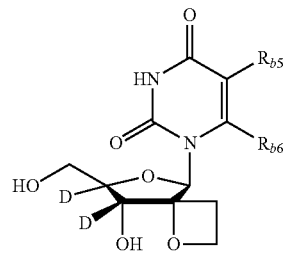

(II-21)
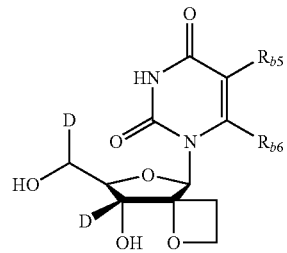

(II-22)
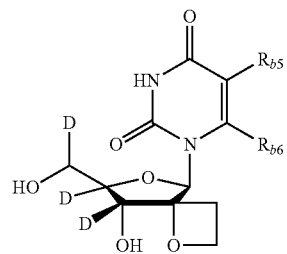

(II-23)
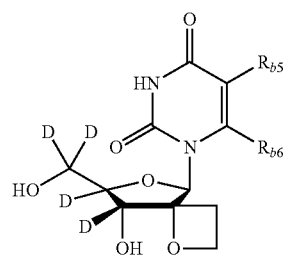

(II-24)
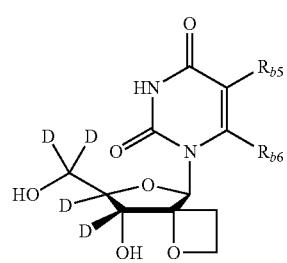

A third embodiment of the invention is a compound represented by Formula III, (III)
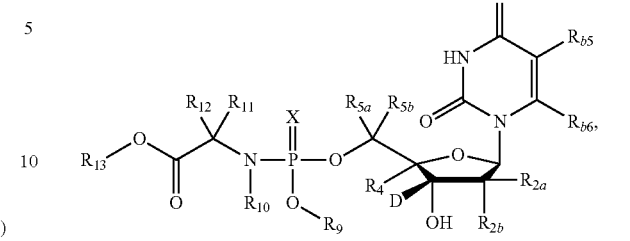

or a pharmaceutically acceptable salt, ester or prodrug thereof, wherein, $R_{2a}$, $R_{2b}$, $R_{b5}$, $R_{b6}$, $R_4$, $R_{5a}$, $R_{5b}$, $R_9$, $R_{10}$, $R_{11}$, $R_{12}$, and $R_{13}$ are as previously defined. X is O or S.

Illustrative structures of formula (III) can be represented, but are not limited, by formula (III-1~III-6):

(III-1)
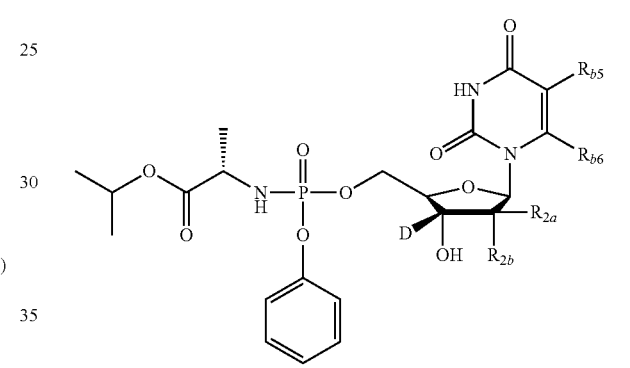

(III-2)
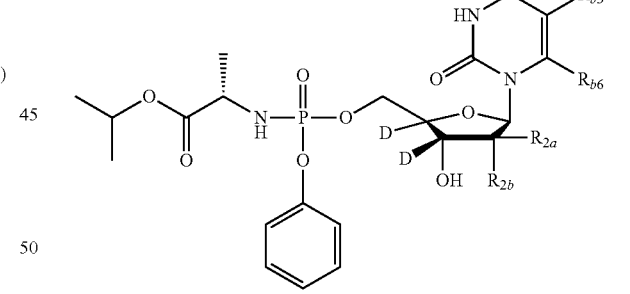

(III-3)
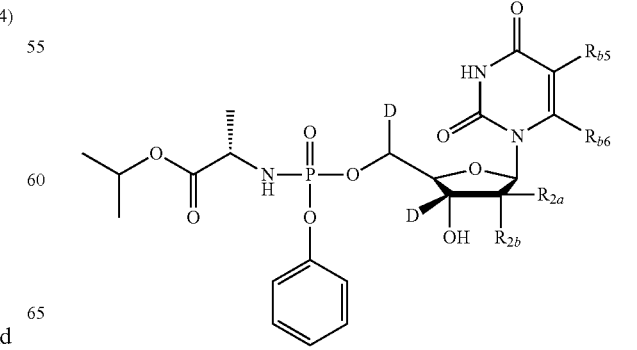

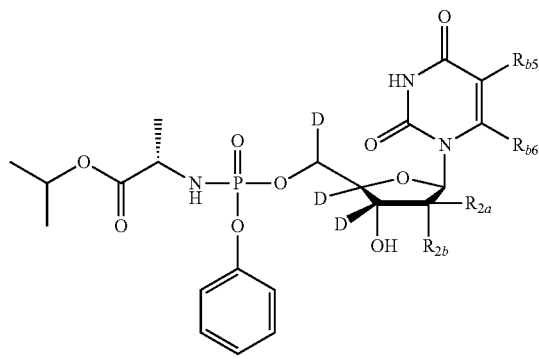

(III-4)

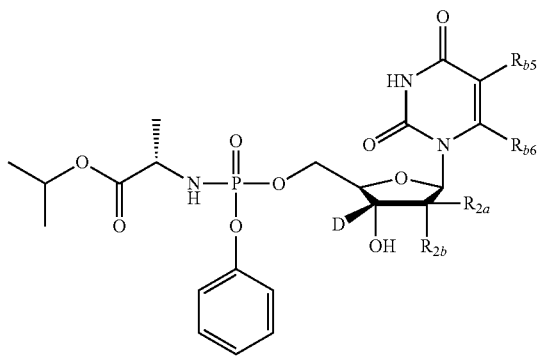

(III-1)

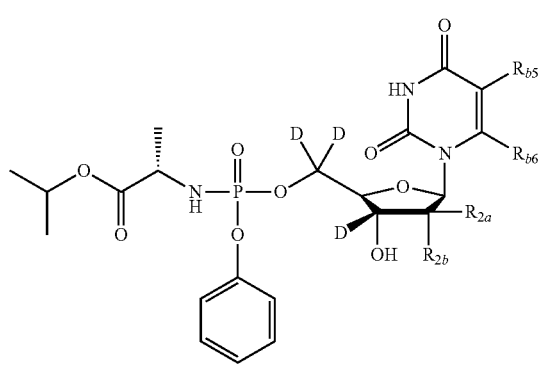

(III-5)

(III-6)

wherein $R_{2a}$, $R_{2b}$, $R_{b5}$, and $R_{b6}$ are as previously defined.

Representative compounds of the invention include, but are not limited to, the following compounds (example 1 to example 20 in Table 1) according to Formula III-1, wherein $R_{2a}$, $R_{2b}$, $R_{b5}$, and $R_{b6}$ are delineated for each example in Table 1.

TABLE 1

| Example | $R_{2a}$ | $R_{2b}$ | $R_{b5}$ | $R_{b6}$ | Example | $R_{2a}$ and $R_{2b}$ | $R_{b5}$ | $R_{b6}$ |
|---|---|---|---|---|---|---|---|---|
| 1 | Me | OH | D | H | 11 | cyclopropyl | D | H |
| 2 | Me | OH | D | D | 12 | cyclopropyl | D | D |
| 3 | Me | OH | CD₃ | H | 13 | cyclopropyl | CD₃ | H |
| 4 | Me | OH | CD₃ | D | 14 | cyclopropyl | CD₃ | D |
| 5 | Me | OH | H | H | 15 | cyclopropyl | H | H |
| 6 | Me | F | D | H | 16 | oxetanyl | D | H |
| 7 | Me | F | D | D | 17 | oxetanyl | D | D |
| 8 | Me | F | CD₃ | H | 18 | oxetanyl | CD₃ | H |

TABLE 1-continued

| Example | $R_{2a}$ | $R_{2b}$ | $R_{b5}$ | $R_{b6}$ | Example | $R_{2a}$ and $R_{2b}$ | $R_{b5}$ | $R_{b6}$ |
|---|---|---|---|---|---|---|---|---|
| 9 | Me | F | CD$_3$ | D | 19 | 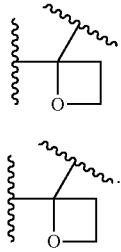 | CD$_3$ | D |
| 10 | Me | F | H | H | 20 | 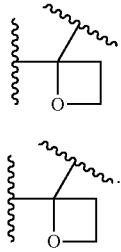 | H | H |

Representative compounds of the invention include, but are not limited to, the following compounds (example 21 to example 40 in Table 2) according to Formula III-2, wherein, $R_{2a}$, $R_{2b}$, $R_{b5}$, and $R_{b6}$ are delineated for each example in Table 2.

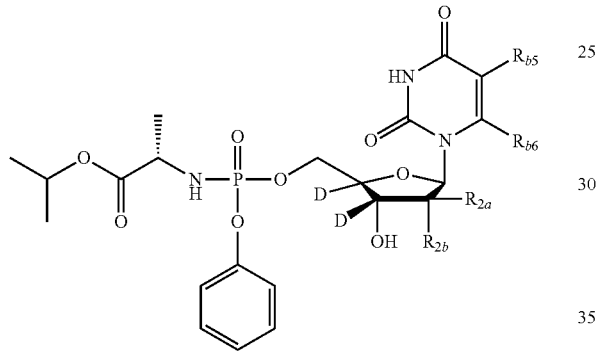

(III-2)

TABLE 2

| Example | $R_{2a}$ | $R_{2b}$ | $R_{b5}$ | $R_{b6}$ | Example | $R_{2a}$ and $R_{2b}$ | $R_{b5}$ | $R_{b6}$ |
|---|---|---|---|---|---|---|---|---|
| 21 | Me | OH | D | H | 31 | 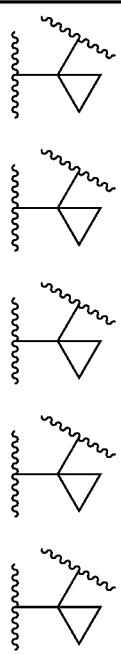 | D | H |
| 22 | Me | OH | D | D | 32 | 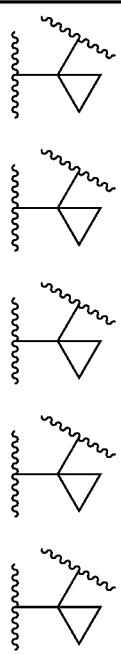 | D | D |
| 23 | Me | OH | CD$_3$ | H | 33 | 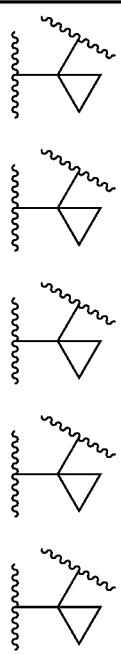 | CD$_3$ | H |
| 24 | Me | OH | CD$_3$ | D | 34 | 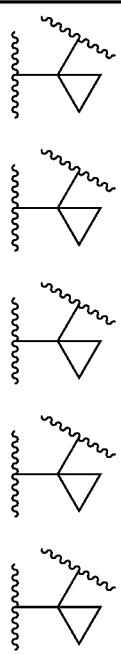 | CD$_3$ | D |
| 25 | Me | OH | H | H | 35 | 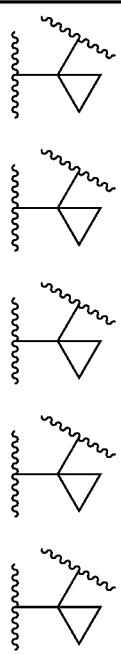 | H | H |
| 26 | Me | F | D | H | 36 | 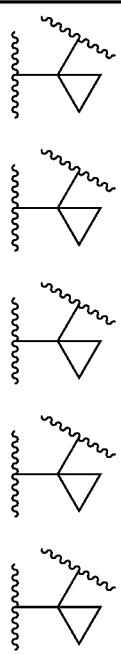 | D | H |
| 27 | Me | F | D | D | 37 | 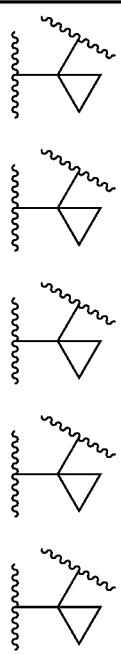 | D | D |
| 28 | Me | F | CD$_3$ | H | 38 | 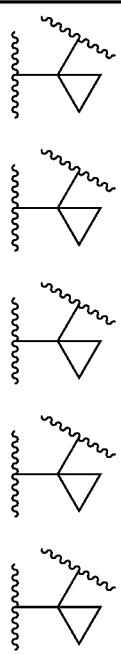 | CD$_3$ | H |
| 29 | Me | F | CD$_3$ | D | 39 | 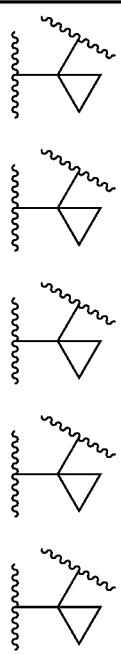 | CD$_3$ | D |
| 30 | Me | F | H | H | 40 | 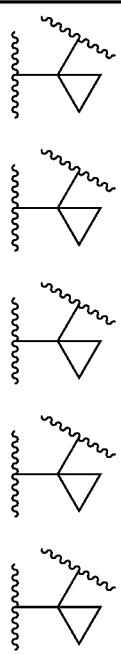 | H | H |

Representative compounds of the invention include, but are not limited to, the following compounds (example 41 to example 60 in Table 3) according to Formula III-3, wherein, $R_{2a}$, $R_{2b}$, $R_{b5}$, and $R_{b6}$ are delineated for each example in Table 3.

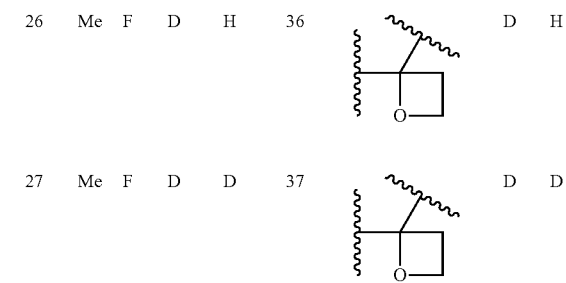

(III-3)

TABLE 3

| Example | R$_{2a}$ | R$_{2b}$ | R$_{b5}$ | R$_{b6}$ | Example | R$_{2a}$ and R$_{2b}$ | R$_{b5}$ | R$_{b6}$ |
|---|---|---|---|---|---|---|---|---|
| 41 | Me | OH | D | H | 51 | (cyclopropyl) | D | H |
| 42 | Me | OH | D | D | 52 | (cyclopropyl) | D | D |
| 43 | Me | OH | CD$_3$ | H | 53 | (cyclopropyl) | CD$_3$ | H |
| 44 | Me | OH | CD$_3$ | D | 54 | (cyclopropyl) | CD$_3$ | D |
| 45 | Me | OH | H | H | 55 | (cyclopropyl) | H | H |
| 46 | Me | F | D | H | 56 | (oxetanyl) | D | H |
| 47 | Me | F | D | D | 57 | (oxetanyl) | D | D |
| 48 | Me | F | CD$_3$ | H | 58 | (oxetanyl) | CD$_3$ | H |
| 49 | Me | F | CD$_3$ | D | 59 | (oxetanyl) | CD$_3$ | D |
| 50 | Me | F | H | H | 60 | (oxetanyl) | H | H |

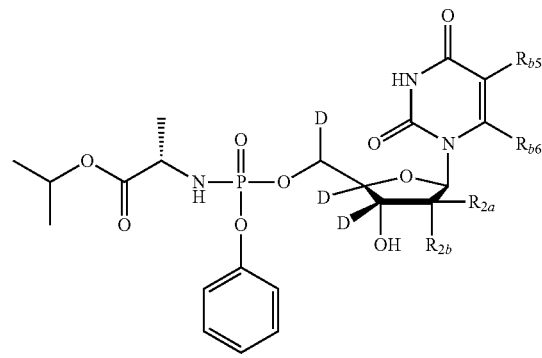

(III-4)

Representative compounds of the invention include, but are not limited to, the following compounds (example 61 to example 80 in Table 4) according to Formula III-4, wherein, R$_{2a}$, R$_{2b}$, R$_{b5}$, and R$_{b6}$ are delineated for each example in Table 4.

TABLE 4

| Example | R$_{2a}$ | R$_{2b}$ | R$_{b5}$ | R$_{b6}$ | Example | R$_{2a}$ and R$_{2b}$ | R$_{b5}$ | R$_{b6}$ |
|---|---|---|---|---|---|---|---|---|
| 61 | Me | OH | D | H | 71 | (cyclopropyl) | D | H |
| 62 | Me | OH | D | D | 72 | (cyclopropyl) | D | D |
| 63 | Me | OH | CD$_3$ | H | 73 | (cyclopropyl) | CD$_3$ | H |
| 64 | Me | OH | CD$_3$ | D | 74 | (cyclopropyl) | CD$_3$ | D |
| 65 | Me | OH | H | H | 75 | (cyclopropyl) | H | H |
| 66 | Me | F | D | H | 76 | (oxetanyl) | D | H |
| 67 | Me | F | D | D | 77 | (oxetanyl) | D | D |
| 68 | Me | F | CD$_3$ | H | 78 | (oxetanyl) | CD$_3$ | H |

TABLE 4-continued

| Example | $R_{2a}$ | $R_{2b}$ | $R_{b5}$ | $R_{b6}$ | Example | $R_{2a}$ and $R_{2b}$ | $R_{b5}$ | $R_{b6}$ |
|---|---|---|---|---|---|---|---|---|
| 69 | Me | F | $CD_3$ | D | 79 | 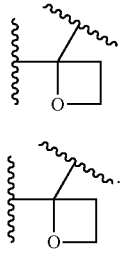 | $CD_3$ | D |
| 70 | Me | F | H | H | 80 | 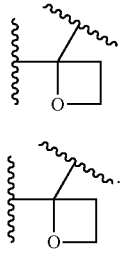 | H | H |

Representative compounds of the invention include, but are not limited to, the following compounds (example 81 to example 100 in Table 5) according to Formula III-5, wherein, $R_{2a}$, $R_{2b}$, $R_{b5}$, and $R_{b6}$ are delineated for each example in Table 5.

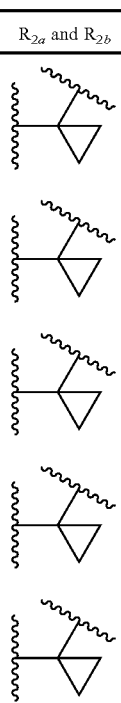

(III-5)

TABLE 5

| Example | $R_{2a}$ | $R_{2b}$ | $R_{b5}$ | $R_{b6}$ | Example | $R_{2a}$ and $R_{2b}$ | $R_{b5}$ | $R_{b6}$ |
|---|---|---|---|---|---|---|---|---|
| 81 | Me | OH | D | H | 91 | cyclopropyl | D | H |
| 82 | Me | OH | D | D | 92 | cyclopropyl | D | D |
| 83 | Me | OH | $CD_3$ | H | 93 | cyclopropyl | $CD_3$ | H |
| 84 | Me | OH | $CD_3$ | D | 94 | cyclopropyl | $CD_3$ | D |
| 85 | Me | OH | H | H | 95 | cyclopropyl | H | H |
| 86 | Me | F | D | H | 96 | oxetanyl | D | H |
| 87 | Me | F | D | D | 97 | oxetanyl | D | D |
| 88 | Me | F | $CD_3$ | H | 98 | oxetanyl | $CD_3$ | H |
| 89 | Me | F | $CD_3$ | D | 99 | oxetanyl | $CD_3$ | D |
| 90 | Me | F | H | H | 100 | oxetanyl | H | H |

Representative compounds of the invention include, but are not limited to, the following compounds (example 101 to example 120 in Table 6) according to Formula III-6, wherein, $R_{2a}$, $R_{2b}$, $R_{b5}$, and $R_{b6}$ are delineated for each example in Table 6.

(III-6)

TABLE 6

| Example | $R_{2a}$ | $R_{2b}$ | $R_{b5}$ | $R_{b6}$ | Example | $R_{2a}$ and $R_{2b}$ | $R_{b5}$ | $R_{b6}$ |
|---|---|---|---|---|---|---|---|---|
| 101 | Me | OH | D | H | 111 | 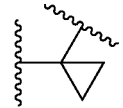 [SMILES: *C1(*)CC1] | D | H |

TABLE 6-continued

| Example | $R_{2a}$ | $R_{2b}$ | $R_{b5}$ | $R_{b6}$ | Example | $R_{2a}$ and $R_{2b}$ | $R_{b5}$ | $R_{b6}$ |
|---|---|---|---|---|---|---|---|---|
| 102 | Me | OH | D | D | 112 | (cyclopropyl) | D | D |
| 103 | Me | OH | $CD_3$ | H | 113 | (cyclopropyl) | $CD_3$ | H |
| 104 | Me | OH | $CD_3$ | D | 114 | (cyclopropyl) | $CD_3$ | D |
| 105 | Me | OH | H | H | 115 | (cyclopropyl) | H | H |
| 106 | Me | F | D | H | 116 | (oxetanyl) | D | H |
| 107 | Me | F | D | D | 117 | (oxetanyl) | D | D |
| 108 | Me | F | $CD_3$ | H | 118 | (oxetanyl) | $CD_3$ | H |
| 109 | Me | F | $CD_3$ | D | 119 | (oxetanyl) | $CD_3$ | D |
| 110 | Me | F | H | H | 120 | (oxetanyl) | H | H |

The term "compound", as used herein in reference to the compounds of Formulas I, II, II-1 to II-24, III and III-1 to III-6, refers to a collection of molecules of identical molecular structure, except for isotopic variation. Atoms within the compounds which are not designated as a specific isotope can be any stable isotope of the indicated element. Typically, the isotopic distribution of each such atom will correspond substantially to the natural isotopic abundance for that element. The designation of an atom as deuterium in the compounds of the invention indicates that this position is enriched with deuterium at a level which is significantly greater than the natural abundance of this isotope. For example, in preferred compounds of the invention, the designation of an atom as deuterium signifies that this position is deuterated in at least 5% of the molecules. Preferably, such a position is deuterated in at least 10, 20, 30, 40 or 50% of the molecules. In certain embodiments, such a position is deuterated in at least 60, 70, 80, 90 or 95% of the molecules. In compounds of the invention having two or more atoms designated as deuterium, and in preferred embodiments all indicated positions are deuterated in at least 5%, 10%, 15%, 20%, 25%, 50%, 60%, 75%, 80% or 90% of the molecules.

The present invention also features pharmaceutical compositions comprising a compound of the invention, or a pharmaceutically acceptable salt, ester or prodrug thereof. In one embodiment, the present invention features pharmaceutical compositions comprising a therapeutically effective amount of a compound of the invention, or a pharmaceutically acceptable salt, ester or prodrug thereof, in combination with a pharmaceutically acceptable carrier or excipient. In another embodiment, the invention features methods of treating a hepatitis C infection in a subject in need of such treatment with said pharmaceutical composition.

In addition, the present invention features methods of using compounds of the present invention or pharmaceutically acceptable salts thereof to treat HCV infection. The methods comprise administering to an HCV patient in need thereof an effective amount of a compound of the invention or a pharmaceutically acceptable salt thereof.

It will be appreciated that the compounds of the present invention may contain one or more asymmetric carbon atoms and may exist in racemic, diastereoisomeric, and optically active forms. It should be understood that the compounds encompassed by the present invention are those that are suitably stable for use as pharmaceutical agent.

Yet a further embodiment of the present invention is a pharmaceutical composition comprising any single compound or a combination of two or more compounds delineated herein, or a pharmaceutically acceptable salt thereof, in combination with one or more agents known in the art, with a pharmaceutically acceptable carrier or excipient. In the methods described herein, a compound of the present invention or a pharmaceutically acceptable salt thereof can be administered alone, or in combination with one or more other anti-HCV agents, such as HCV polymerase inhibitors, HCV protease inhibitors, HCV NS5A inhibitors, CD81 inhibitors, cyclophilin inhibitors, internal ribosome entry site (IRES) inhibitors or any combinations thereof. Interferon, ribavirin or both can also be included in the treatment. For example, the methods described herein can further comprise administering to the patient peginterferon-alpha and ribavirin. Different agents can be administered simultaneously or sequentially. The dosing frequency of each agent in a treatment regimen can be the same or different. For instance, a compound of the invention can be dosed once daily and ribavirin can be dosed twice daily.

Compounds of the present invention can be administered as the sole active pharmaceutical agent, or used in combination with one or more agents to treat or prevent hepatitis C infections or the symptoms associated with HCV infection. Other agents to be administered in combination with a compound or combination of compounds of the invention include therapies for disease caused by HCV infection that suppresses HCV viral replication by direct or indirect mechanisms. These include agents such as host immune modulators (for example, interferon-alpha, pegylated interferon-alpha, interferon-beta, interferon-gamma, CpG oligonucleotides and the like), cyclophilins (e.g., Debio 025), or antiviral compounds that inhibit host cellular functions such as inosine monophosphate dehydrogenase (for example, ribavirin and the like). Also included are cytokines that modulate immune function. Also included are vaccines comprising HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like. Other agents to be administered in combination with a compound of the present invention include any agent or combination of agents that inhibit the replication of HCV by targeting proteins of the viral genome involved in the viral replication. These agents include but are not limited to other inhibitors of HCV RNA dependent RNA polymerase such as, for example, nucleoside type polymerase inhibitors described in WO0190121 (A2) or U.S. Pat. No. 6,348,587 B1 or WO0160315 or WO0132153 or non-nucleoside inhibitors such as, for example, benzimidazole polymerase inhibitors described in EP 1162196A1 or WO0204425 or inhibitors of HCV protease such as, for example, peptidomimetic type inhibitors such as BILN2061 and the like or inhibitors of HCV helicase.

Other agents to be administered in combination with a compound of the present invention include any agent or combination of agents that inhibit the replication of other viruses for co-infected individuals. These agents include but are not limited to therapies for disease caused by hepatitis B (HBV) infection or therapies for disease caused by human immunodeficiency virus (HIV) infection.

Accordingly, one aspect of the invention is directed to a method for treating or preventing an infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of the invention, or a pharmaceutically acceptable salt, stereoisomer, tautomer, prodrug, salt of a prodrug, or combination thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

A further aspect of the invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the invention, or a pharmaceutically acceptable salt, stereoisomer, tautomer, prodrug, salt of a prodrug, or combination thereof. Yet another aspect of the invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the invention, or a pharmaceutically acceptable salt, stereoisomer, tautomer, prodrug, salt of a prodrug, or combination thereof. An agent that treats patients for disease caused by hepatitis B (HBV) infection may be for example, but not limited thereto, L-deoxythymidine, adefovir, lamivudine or tenfovir, or any combination thereof. An example of the RNA-containing virus includes, but not limited to, hepatitis C virus (HCV).

Another aspect of the invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the invention, or a pharmaceutically acceptable salt, stereoisomer, tautomer, prodrug, salt of a prodrug, or combination thereof. An example of the RNA-containing virus includes, but not limited to, hepatitis C virus (HCV). In addition, the present invention provides the use of a compound or a combination of compounds of the invention, or a therapeutically acceptable salt form, stereoisomer, or tautomer, prodrug, salt of a prodrug, or combination thereof, and one or more agents selected from the group consisting of a host immune modulator and a second antiviral agent, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

When used in the above or other treatments, combination of compound or compounds of the invention, together with one or more agents as defined herein above, can be employed in pure form or, where such forms exist, in pharmaceutically acceptable salt form, prodrug, salt of a prodrug, or combination thereof. Alternatively, such combination of therapeutic agents can be administered as a pharmaceutical composition containing a therapeutically effective amount of the compound or combination of compounds of interest, or their pharmaceutically acceptable salt form, prodrugs, or salts of the prodrug, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, further aspect of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt, stereoisomer, or tautomer, prodrug, salt of a prodrug, or combination thereof, one or more agents as defined hereinabove, and a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including but not limited to, agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to, ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to, interferons conjugated with other proteins including but not limited to, human albumin. Class I interferons are a group of interferons that all bind to receptor type I, including both naturally and synthetically produced class I interferons, while class II interferons all bind to receptor type II. Examples of class I interferons include, but are not limited to, [alpha]-, [beta]-, [delta]-, [omega]-, and [tau]-interferons, while examples of class II interferons include, but are not limited to, [gamma]-interferons.

Inhibitors of HCV NS3 protease include agents (compounds or biologicals) that are effective to inhibit the function of HCV NS3 protease in a mammal Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085, WO 2006/007700 and WO 2006/007708 (all by Boehringer Ingelheim), WO 02/060926, WO 03/053349, WO03/099274, WO 03/099316, WO 2004/032827, WO 2004/043339, WO 2004/094452, WO 2005/046712, WO 2005/051410, WO 2005/054430 (all by BMS), WO 2004/072243, WO 2004/093798, WO 2004/113365, WO 2005/010029 (all by Enanta), WO 2005/037214 (Intermune) and WO 2005/051980 (Schering), and the candidates identified as VX-950, ITMN-191 and SCH 503034.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388 and WO 2006/007693 (all by Boehringer Ingelheim), WO 2005/049622 (Japan Tobacco), WO 2005/014543 (Japan Tobacco), WO 2005/012288 (Genelabs), WO 2004/087714 (IRBM), WO 03/101993 (Neogenesis), WO 03/026587 (BMS), WO 03/000254 (Japan Tobacco), and WO 01/47883 (Japan Tobacco), and the clinical candidates XTL-2125, HCV 796, R-1626 and NM 283.

Inhibitors of another target in the HCV life cycle include agents (compounds or biologicals) that are effective to inhibit the formation and/or replication of HCV other than by inhibiting the function of the HCV NS3 protease. Such agents may interfere with either host or HCV viral mechanisms necessary for the formation and/or replication of HCV Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to, an NS5A protein and an NS4B protein.

It can occur that a patient may be co-infected with hepatitis C virus and one or more other viruses, including but not limited to, human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

According to yet another embodiment, the pharmaceutical compositions of the present invention may further comprise inhibitor(s) of other targets in the HCV life cycle, including, but not limited to, helicase, polymerase, metalloprotease, and internal ribosome entry site (IRES).

According to still another embodiment, the present invention includes methods of treating viral infection such as, but not limited to, hepatitis C infections in a subject in need of such treatment by administering to said subject an effective amount of a compound of the present invention or a pharmaceutically acceptable salt, ester, or prodrug thereof.

According to a further embodiment, the present invention includes methods of treating hepatitis C infections in a subject in need of such treatment by administering to said subject an anti-HCV virally effective amount or an inhibitory amount of a pharmaceutical composition of the present invention.

An additional embodiment of the present invention includes methods of treating biological samples by contacting the biological samples with the compounds of the present invention.

Yet a further aspect of the present invention is a process of making any of the compounds delineated herein employing any of the synthetic means delineated herein.

DEFINITIONS

Listed below are definitions of various terms used to describe this invention. These definitions apply to the terms as they are used throughout this specification and claims, unless otherwise limited in specific instances, either individually or as part of a larger group.

The term "viral infection" refers to the introduction of a virus into cells or tissues, e.g., hepatitis C virus (HCV). In general, the introduction of a virus is also associated with replication. Viral infection may be determined by measuring virus antibody titer in samples of a biological fluid, such as blood, using, e.g., enzyme immunoassay. Other suitable diagnostic methods include molecular based techniques, such as RT-PCR, direct hybrid capture assay, nucleic acid sequence based amplification, and the like. A virus may infect an organ, e.g., liver, and cause disease, e.g., hepatitis, cirrhosis, chronic liver disease and hepatocellular carcinoma.

The term "immune modulator" refers to any substance meant to alter the working of the humoral or cellular immune system of a subject. Such immune modulators include inhibitors of mast cell-mediated inflammation, interferons, interleukins, prostaglandins, steroids, cortico-steroids, colony-stimulating factors, chemotactic factors, etc.

The term "alkyl", as used herein, refers to a saturated, monovalent straight- or branched-chain hydrocarbongroup. Preferred alkyl radicals include $C_1$-$C_6$ alkyl and $C_1$-$C_8$ alkyl radicals. Examples of $C_1$-$C_6$ alkyl groups include, but are not limited to, methyl, ethyl, propyl, isopropyl, n-butyl, tert-butyl, neopentyl, n-hexyl groups; and examples of $C_1$-$C_8$ alkyl groups include, but are not limited to, methyl, ethyl, propyl, isopropyl, n-butyl, tert-butyl, neopentyl, n-hexyl, heptyl, and octyl groups.

The term "alkenyl", as used herein, denote a monovalent group derived from a hydrocarbon moiety by the removal of a single hydrogen atom wherein the hydrocarbon moiety has at least one carbon-carbon double bond. Preferred alkenyl groups include $C_2$-$C_6$ alkenyl and $C_2$-$C_8$ alkenyl groups. Alkenyl groups include, but are not limited to, for example, ethenyl, propenyl, butenyl, 1-methyl-2-buten-1-yl, heptenyl, octenyl and the like.

The term "alkynyl", as used herein, denotes a monovalent group derived from a hydrocarbon moiety by the removal of a single hydrogen atom wherein the hydrocarbon moiety has at least one carbon-carbon triple bond. Preferred alkynyl groups include $C_2$-$C_6$ alkynyl and $C_2$-$C_8$ alkynyl groups. Representative alkynyl groups include, but are not limited to, for example, ethynyl, 1-propynyl, 1-butynyl, heptynyl, octynyl and the like.

The term "carbocycle" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. Where a carbocycle group is a divalent moiety linking two other elements in a depicted chemical structure (such as Z in Formula $I_A$), the carbocycle group can be attached to the two other elements through any two substitutable ring atoms. A $C_4$-$C_6$ carbocycle has 4-6 ring atoms.

The term "cycloalkyl", as used herein, denotes a monovalent group derived from a monocyclic or polycyclic saturated carbocyclic ring compound by the removal of a single hydrogen atom. Preferred cycloalkyl groups include $C_3$-$C_8$ cycloalkyl and $C_3$-$C_{12}$ cycloalkyl groups Examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The term "cycloalkenyl" as used herein, denote a monovalent group derived from a monocyclic or polycyclic carbocyclic ring compound having at least one carbon-carbon double bond by the removal of a single hydrogen atom. Preferred cycloalkenyl groups include $C_3$-$C_8$ cycloalkenyl and $C_3$-$C_{12}$ cycloalkenyl groups. Examples of $C_3$-$C_8$-cycloalkenyl include, but are not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "aryl," as used herein, refers to a mono- or bicyclic carbocyclic ring system having one or two aromatic rings including, but not limited to, phenyl, naphthyl, tetrahydronaphthyl, indanyl, indenyl and the like.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "heteroaryl," as used herein, refers to a mono-, bi-, or tri-cyclic aromatic radical or ring having from five to ten ring atoms of which at least one ring atom is selected from S, O and N; wherein any N or S contained within the ring may be optionally oxidized. Preferred heteroaryl groups are monocyclic or bicyclic. Heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroarylalkyl," as used herein, refers to a $C_1$-$C_3$ alkyl or $C_1$-$C_6$ alkyl residue attached to a heteroaryl ring. Examples include, but are not limited to, pyridinylmethyl, pyrimidinylethyl and the like.

The term "substituted" as used herein, refers to independent replacement of one, two, or three or more of the hydrogen atoms thereon with substituents including, but not limited to, —F, —Cl, —Br, —I, —OH, protected hydroxy, —NO$_2$, —CN, —NH$_2$, N$_3$, protected amino, alkoxy, thioalkoxy, oxo, -halo-C$_1$-C$_{12}$-alkyl, -halo-C$_2$-C$_{12}$-alkenyl, -halo-C$_2$-C$_{12}$-alkynyl, -halo-C$_3$-C$_{12}$-cycloalkyl, —NH—C$_1$-C$_{12}$-alkyl, —NH—C$_2$-C$_{12}$-alkenyl, —NH—C$_2$-C$_{12}$-alkynyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkynyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkynyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkynyl, —NHC(NH)—C$_3$-C$_{12}$-cycloalkyl, —NHC(NH)-aryl, —NHC(NH)- heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, methylthiomethyl, or -L'—R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —$NO_2$, —CN, or —$NH_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

The term "heterocycloalkyl" and "heterocyclic" can be used interchangeably and refer to a non-aromatic 3-, 4-, 5-, 6- or 7-membered ring or a bi- or tri-cyclic group fused system, where: (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (v) any of the above rings may be fused to a benzene ring, and (vi) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted to give substituted heterocyclic.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, hetoerarylalkylene and heterocycloalkylene groups are to be included in the above definitions, and are applicable to provide the formulas herein with proper valency.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "activated hydroxy", as used herein, refers to a hydroxy group activated with a hydroxy activating group, as defined above, including mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups.

The terms "halo" and "halogen," as used herein, refer to an atom selected from fluorine, chlorine, bromine and iodine.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T.H. Greene and P.G., S. M. Wuts, Protective Groups in Organic Synthesis, 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$). Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkanoate having from 1 to 6 carbon atoms, sulfonate and aryl sulfonate.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T.H. Greene and P.G. M. Wuts, Protective Groups in Organic Synthesis, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al., (ed.), Methods in Enzymology, Vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations,* VCH Publishers (1989); T. W. Greene and P.G.M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Antiviral Activity

An inhibitory amount or dose of the compounds of the present invention may range from about 0.01 mg/Kg to about 500 mg/Kg, alternatively from about 1 to about 100 mg/Kg Inhibitory amounts or doses will also vary depending on route of administration, as well as the possibility of co-usage with other agents.

According to the methods of treatment of the present invention, viral infections are treated or prevented in a subject such as a human or lower mammal by administering to the subject an anti-hepatitis C virally effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

The term "anti-hepatitis C virally effective amount" of a compound of the invention, as used herein, mean a sufficient amount of the compound so as to decrease the viral load in a biological sample or in a subject (e.g., resulting in at least 10%, preferably at least 50%, more preferably at least 80%, and most preferably at least 90% or 95%, reduction in viral load). As well understood in the medical arts, an anti-hepatitis C virally effective amount of a compound of this invention will be at a reasonable benefit/risk ratio applicable to any medical treatment.

The term "inhibitory amount" of a compound of the present invention means a sufficient amount to decrease the hepatitis C viral load in a biological sample or a subject (e.g., resulting in at least 10%, preferably at least 50%, more preferably at least 80%, and most preferably at least 90% or 95%, reduction in viral load). It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof; or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
ACN for acetonitrile;
BME for 2-mercaptoethanol;
BOP for benzotriazol-1-yloxy-tris(dimethylamino)phosphonium hexafluorophosphate;
BzCl for benzoyl chloride;
CDI for carbonyldiimidazole;
COD for cyclooctadiene;
DABCO for 1,4-diazabicyclo[2.2.2]octane;
DAST for diethylaminosulfur trifluoride;
DABCYL for 6-(N-4'-carboxy-4-(dimethylamino)azobenzene)-aminohexyl-1-O-(2-cyanoethyl)-(N,N-diisopropyl)-phosphoramidite;
DBU for 1,8-Diazabicycloundec-7-ene;
DCC for N,N'-dicyclohexylcarbodiimide;
DCM for dichloromethane;
DIAD for diisopropyl azodicarboxylate;
DIBAL-H for diisobutylaluminum hydride;
DIPEA for diisopropyl ethylamine;
DMAP for N,N-dimethylaminopyridine;
DME for ethylene glycol dimethyl ether;
DMEM for Dulbecco's Modified Eagles Media;
DMF for N,N-dimethyl formamide;
DMSO for dimethylsulfoxide;
DSC for N, N'-disuccinimidyl carbonate;
DUPHOS for

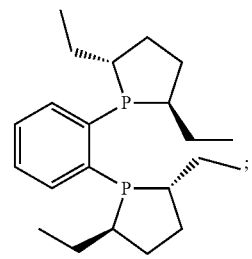 [SMILES: CC[C@@H]1CC[C@@H](CC)P1c1ccccc1P1[C@H](CC)CC[C@H]1CC]

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
EtOH for ethyl alcohol;
HATU for O(7-Azabenzotriazole-1-yl)-N,N,N',N'-tetramethyluronium hexafluorophosphate;
HCl for hydrochloric acid;
Hoveyda's Cat. for Dichloro(o-isopropoxyphenylmethylene) (tricyclohexylphosphine)ruthenium(II);
In for indium;
KHMDS is potassium bis(trimethylsilyl)amide;
Ms for mesyl;
NMM for N-4-methylmorpholine;
NMI for N-methylimidazole;
NMO for N-4-methylmorpholine-N-Oxide;
PyBrOP for Bromo-tri-pyrolidino-phosphonium hexafluorophosphate;
Ph for phenyl;
RCM for ring-closing metathesis;
RT for reverse transcription;
RT-PCR for reverse transcription-polymerase chain reaction;
TBME for tert-butyl methyl ether;
TEA for triethyl amine;

Tf$_2$O for trifluoromethanesulfonic anhydride;
TFA for trifluoroacetic acid;
THF for tetrahydrofuran;
TLC for thin layer chromatography;
(TMS)$_2$NH for hexamethyldisilazane;
TMSOTf for trimethylsilyl trifluoromethanesulfonate;
TPAP tetrapropylammonium perruthenate;
TPP or PPh$_3$ for triphenylphosphine;
TrCl for trityl chloride;
DMTrCl for 4,4'-dimethoxytrityl chloride;
tBOC or Boc for tert-butyloxy carbonyl;
Xantphos for 4,5-Bis-diphenylphosphanyl-9,9-dimethyl-9H-xanthene; and
Zhan 1 B for

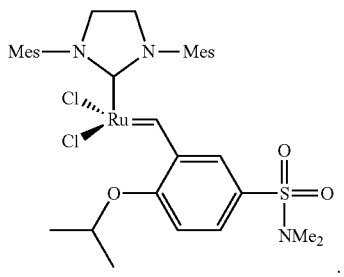

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

One approach to the synthesis of 3'-deuterated compounds of Formula II is exemplified in Scheme 1, wherein R$_{2a}$, R$_{2b}$, R$_{b5}$, R$_{b6}$, R$_{5a}$, R$_{5b}$ and R$_4$ are as previously defined. The compound of formula (1-1) is converted to compound of formula (1-2) by selective protection of 5'-OH of compound of formula (1). The protecting group can be, but not limited to, benzyl, TMS, TBS, or TES. The preferred protecting group is TBS. The protection reaction is conducted in aprotic solvent and in the presence of suitable base. The aprotic solvent can be, but not limited to, DMF, DCM, THF, pyridine or the mixture of. The suitable base can be, but not limited to, TEA, DIPEA, DMAP and pyridine. A more detailed discussion of the procedures, reagents and conditions for protection and deprotection is described in literature, for example, by T.W. Greene and P.G.M. Wuts in "*Protective Groups in Organic Synthesis*" 3$^{rd}$ ed., John Wiley & Son, Inc., 1999. Then, the compound of formula (1-2) is converted to the compound of formula (1-3) by oxidation of 3'-OH to 3'-ketone. The oxidation reagent can be, but not limited to, PCC, PDC, Dess-Matin reagent. A thorough discussion of oxidation transformation reactions is described in literature, for example, by Richard C. Larock in "*Comprehensive Organic Transformations*" 2$^{nd}$ ed., John Wiley & Son, Inc., 1999. The 3'-deuterated compound of formula (1-4) is prepared from the compound of formula (1-3) by reduction using deuterated reducing agent. The deuterated agent can be, but is not limited to, NaBD$_4$ or LiBD$_4$.

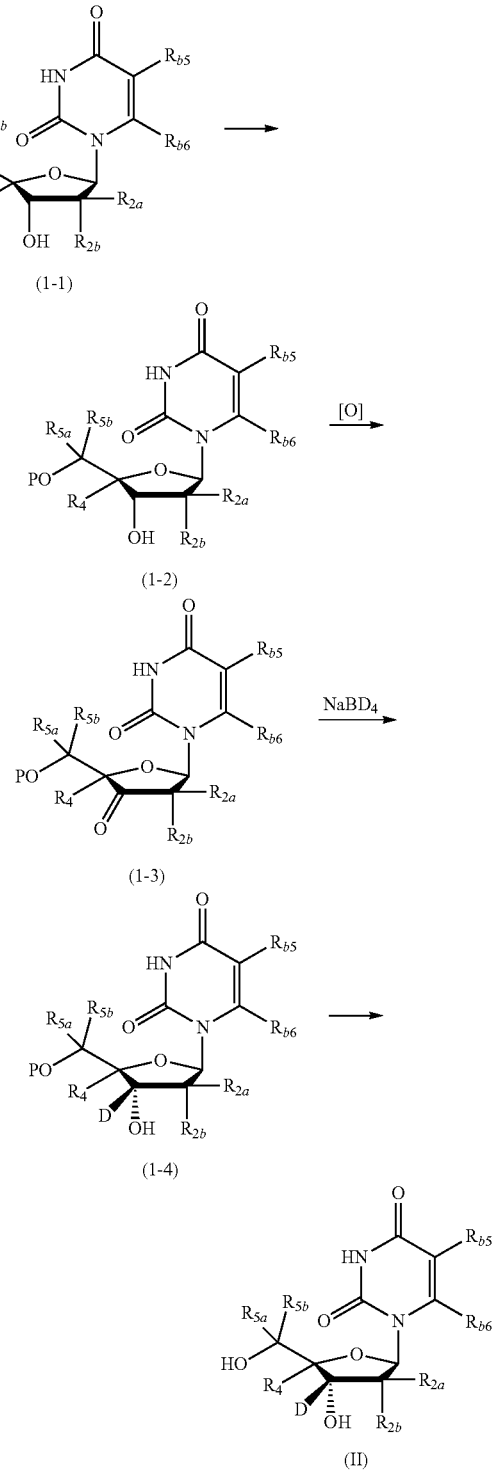

Scheme 1

Deprotection of 5'-protecting group of compound of formula (1-4) to afford the compound of formula (II).

The scheme 2 illustrates the process to prepare 4'-deuterated nucleoside compound of formula (II), wherein R$_{2a}$, R$_{2b}$, $R_{b5}$, $R_{b6}$, $R_{5a}$ and $R_{5b}$ are as previously defined. The compound of formula (2-1) is converted to the compound of formula (2-2) by a few protection and deprotection reactions. Thus, the 5'-OH of the compound of formula (2-1) is protected with a protecting group which can be deprotected in acidic deprotection condition. Such protecting group can be, but not limited to, Boc, trityl. Then the 3'-OH is protected with a protecting group which is stable in acidic deprotection condition. Such protecting group can be, but not limited to TBS. Then deprotection of 5'-OH in acidic condition to give the compound of formula (2-2). A more detailed discussion of the procedures, reagents and conditions for protection and deprotection is described in literature, for example, by T.W. Greene and P.G.M. Wuts in "*Protective Groups in Organic Synthesis*" 3$^{rd}$ ed., John Wiley & Son, Inc., 1999.

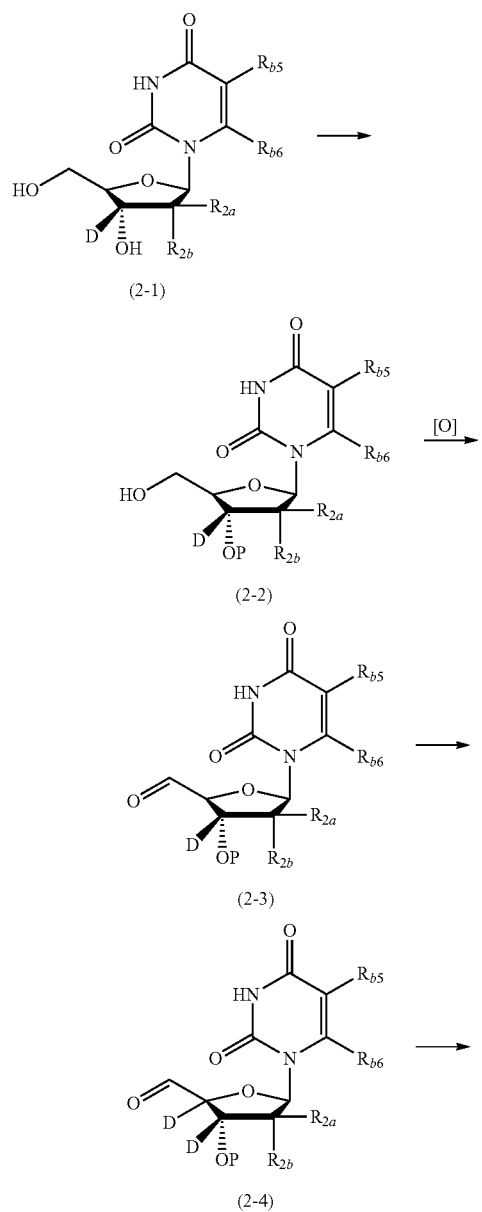

Scheme 2

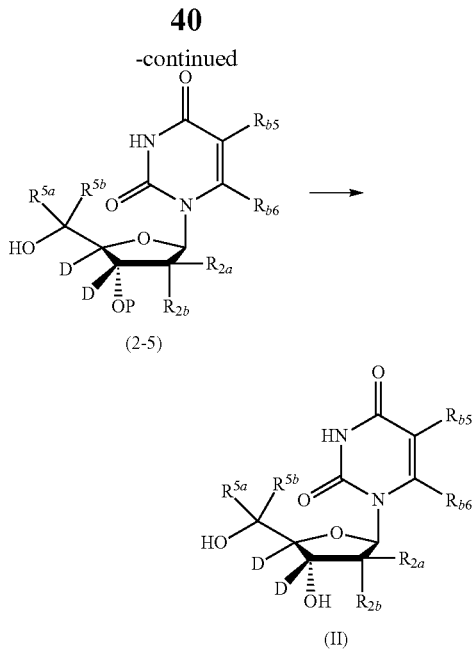

The compound of formula (2-2) is converted to the compound of formula (2-3) by oxidation of 5'-OH to corresponding aldehyde. Then deuterium exchange in $D_2O$ in the presence of base to give the compound of formula (2-4). Such base can be, but not limited to pyridine, TEA, DMAP and $K_2CO_3$. The compound of formula (2-4) is converted to the compound of formula (2-5) by reduction using deuterated or non-deuterated reducing agent. Such reducing agent can be, but not limited to $NaBH_4$, $NaBD_4$, $LiBH_4$ and $LiBD_4$. Then deprotection of 3'-protecting group of compound of formula (2-5) to give the compound of formula (II).

A process to prepare 5'-di-deuterated compound of formula (II) is shown in scheme 3. The compound of formula (3-1) is converted to the compound of formula (3-2) using the similar procedure which is used in the conversion of the compound of formula (2-1) to the compound of formula (2-2). Then the compound of formula (3-2) is converted to the compound of formula (3-3) by oxidation of 5'-OH of compound of formula (3-2) to the corresponding ester. The 5'-di-deuterated compound of formula (3-4) is prepared by reduction of the ester of compound of formula (3-3) with deuterated reducing agent such as, but not limited to $NaBD_4$. Then deprotection of 3'-protecting group to give the compound of formula (II).

Scheme 3

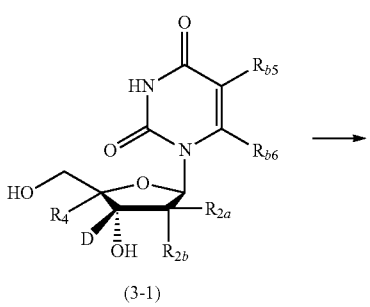

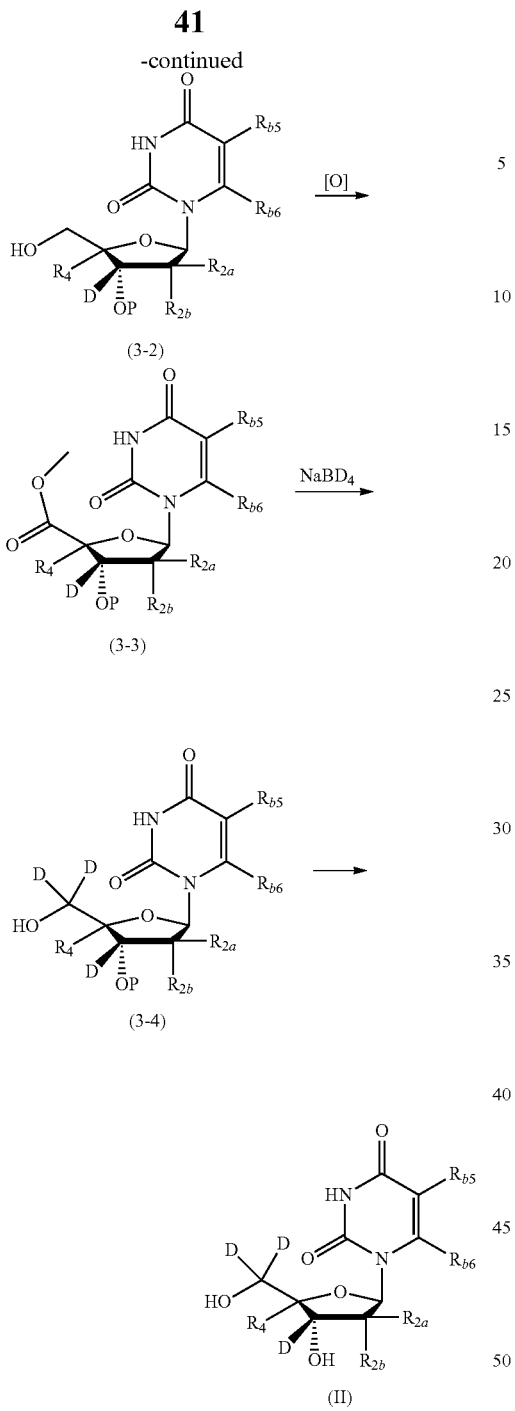

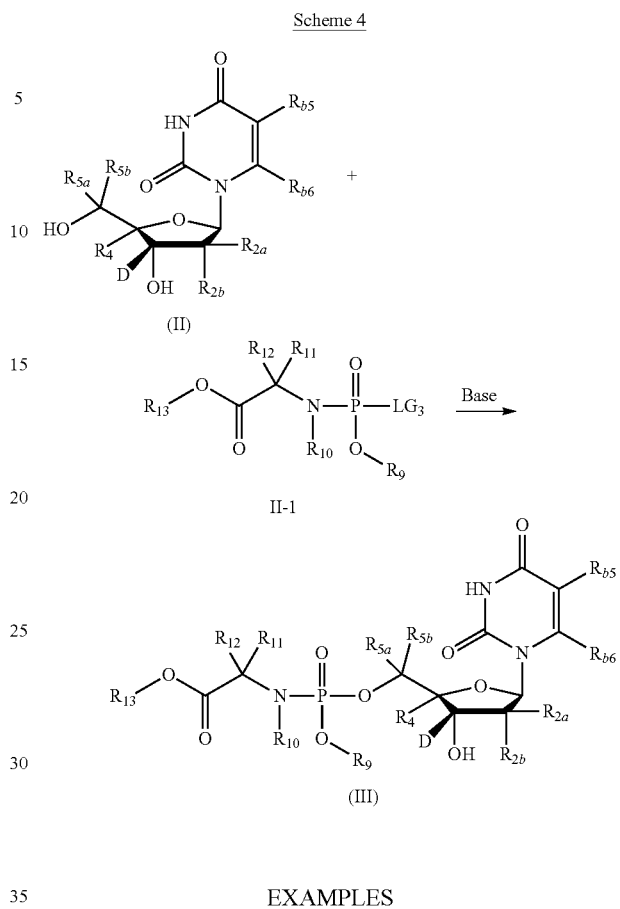

The above schemes showed the processes to prepared 3'-deuterated, 4'-deuterated and 5'-mono/di-deuterated nucleoside compounds. Also these processes can be used separately or together to prepare selective deuterated nucleoside compounds and full deuterated nucleoside compounds on 3',4' and 5' positions.

The preparation of phosphoamidate prodrug is illustrated in scheme 4. The compound of formula III could be synthesized by coupling of nucleoside compound of formula II with phosphoamidate compound II-1 in the presence of organic/inorganic base such as, but not limited to, NMI, DIEPA, TEA, DMAP and iPrMgCl. $LG_3$ is a leaving group such as, but not limited to, Cl or pentafluorophenoxy.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

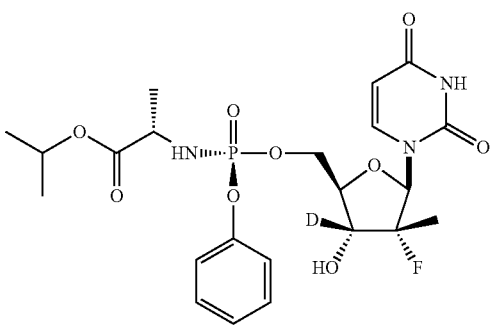 [SMILES: [2H][C@@]1(O)[C@@H](CO[P@@](=O)(N[C@@H](C)C(=O)OC(C)C)Oc2ccccc2)O[C@@H](n2ccc(=O)[nH]c2=O)[C@]1(C)F]

Step 1-1

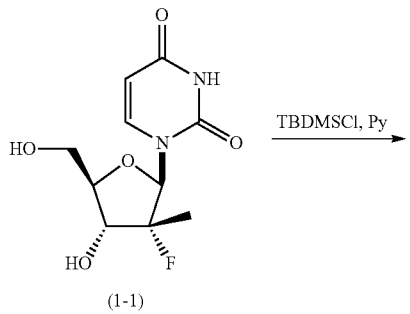

To a stirred solution of 2'-deoxy-2'-fluoro-2'-C-methyluridine (1-1) (5 g, 19.21 mmol.) in dry pyridine (77 mL), was added portionwise TBDMSCl (6.37 g, 42.3 mmol.) at rt. The reaction was stirred at room temperature for 24 h. MeOH (7.77 mL, 192 mmol.) was added to the reaction mixture and it was allowed to stir for 10 min at rt. Then the solvent was removed under reduced pressure. Water (50 mL) was added to the reaction mixture. The mixture extracted with ethyl acetate (2×50 mL), washed with water (50 mL). The organic layer was dried over anhydrous sodium sulfate. After filtration, ethyl acetate was distilled off and the residue obtained was co-evaporated with toluene (twice) to give crude compound (1-2) (7.15 g, 99% yield). $^1$H NMR (500 MHz, CD$_3$OD) δ 8.07 (d, J=8.0 Hz, 1H), 6.15 (d, J=18.0 Hz, 1H), 5.65 (d, J=8.0 Hz, 1H), 4.17 (d, J=12.0 Hz, 1H), 4.08-3.90 (m, 3H), 1.38 (d, J=22.0 Hz, 3H), 0.99 (s, 9H), 0.19 (s, 3H), 0.18 (s, 3H).

Step 1-2

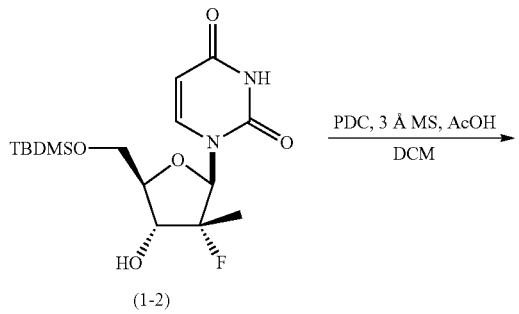

To a slurry of compound (1-2) (3.9 g, 10.41 mmol.) and freshly ground 3 Å MS (8 g) in DCM (104 mL) at rt, was added pyridinium dichromate (4.31 g, 11.46 mmol.) and acetic acid (0.596 mL, 10.41 mmol.). The mixture was stirred at room temperature. The reaction was monitored by $^1$HNMR. Upon the complete conversion of starting material (about 6 h), the reaction mixture was diluted by Et$_2$O and filtered through a short pad of silica gel. The pad of silica gel was washed by Et$_2$O until the most of product was eluted out. The filtrate was concentrated and dried under vacuum to give the ketone compound (1-3) (3.67 g, 94% yield) as a mild yellow solid. $^1$H NMR (500 MHz, CDCl$_3$) δ 8.13 (s, 1H), 7.77 (d, J=8.0 Hz, 1H), 6.31 (d, J=17.0 Hz, 1H), 5.76 (dd, J=8.0, 2.0 Hz, 1H), 4.48 (s, 1H), 4.06 (ddd, J=25.5, 11.5, 2.5 Hz, 2H), 1.38 (d, J=23.5 Hz, 3H), 0.90 (s, 9H), 0.11 (s, 3H), 0.08 (s, 3H).

Step 1-3

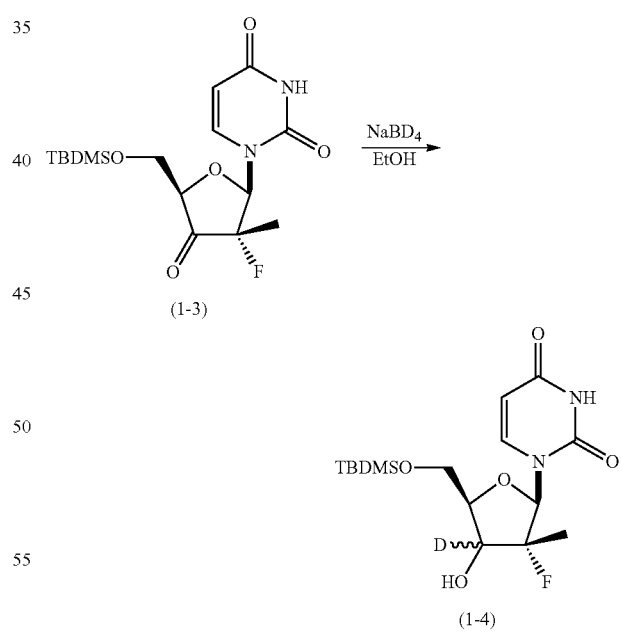

To a solution of ketone compound (1-3)(0.286 g, 0.768 mmol.) in EtOH at 0° C., was added sodium borodeuteride (0.096 g, 2.304 mmol.). The mixture was stirred at 0° C. for 2 h. The reaction was quenched by addition of MeOH (3 mL) at rt. The solvent was removed. The mixture was pardoned between EtOAc and Sat. NH$_4$Cl. The organic layer was washed by brine, dried over Na$_2$SO$_4$, filtered and concentrated to give a crude 3'-deuterated nucleoside compound (1-4) (311 mg) as a mixture of two diastereomers (d.r.=~1:1). MS (ESI): m/e 376.26 (M+1), 398.25 (M+23).

Step 1-4

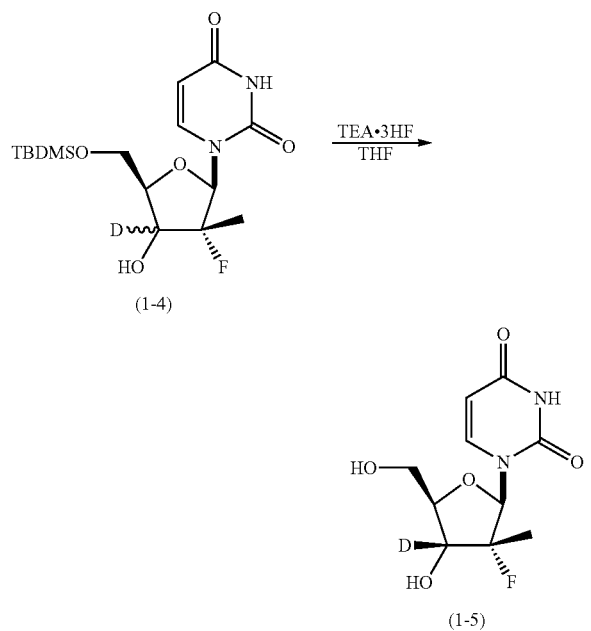

(1-4)

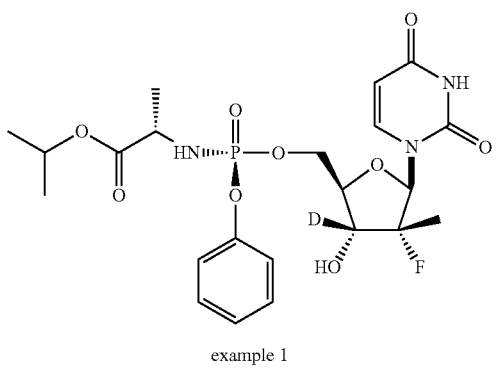

example 1

To a solution of compound (1-5) (0.025 g, 0.096 mmol.) in THF (0.532 mL) at 0° C., was added tert-butylmagnesium chloride (1M, in THF) (0.201 mL, 0.201 mmol.) dropwise. The resulted slurry was stirred at room temperature for 15 min. The mixture was cooled down to 0° C. A solution of (S)-2-[(S)-(2,3,4,5,6-pentafluorophenoxy)-phenoxyphosphorylamino]propionic acid iso-propyl ester (0.078 g, 0.172 mmol.) in THF (0.45 mL) was added into the slurry. The mixture was stirred at 0° C. to room temperature for 16 h. The reaction was quenched by addition of sat. NaHCO$_3$ and diluted by EtOAc(15 mL). The organic layer was separated and washed by brine, dried over Na$_2$SO$_4$, filtered, concentrated to give a crude product. The crude product was purified by prepHPLC to give the title compound of example 1 (0.017 g, 0.032 mmol., 33.5% yield) as a white solid. MS (ESI): m/e 531.26 (M+1). $^1$H NMR (500 MHz, CDCl$_3$) δ 7.99 (s, 1H), 7.44 (d, J=7.5 Hz, 1H), 7.36-7.17 (m, 5H), 6.16 (d, J=19.5 Hz, 1H), 5.68 (d, J=7.5 Hz, 1H), 5.03-4.98 (m, 1H), 4.54-4.50 (m, 1H), 4.45-4.40 (m, 1H), 4.08 (s, 1H), 3.94-3.90 (m, 1H), 3.66-3.62 (m, 1H), 3.35 (s, 1H), 1.41 (d, J=22.5 Hz, 3H), 1.34 (d, J=7.0 Hz, 3H), 1.23 (d, J=5.5 Hz, 6H).

To the solution of compound (1-4) (0.164 g, 93% weight purity, 0.406 mmol.) in THF (8.7 mL) at rt, was added triethylamine tris-hydrofluoride (0.213 mL, 1.310 mmol.) and stirred at room temperature overnight. The solvent was removed. The crude mixture was purified by combiflash (silica gel, 0-7% MeOH in DCM) to give the compound (1-5) (0.059 g, 56% yield). $^1$H NMR (500 MHz, CD$_3$OD) δ 8.01 (d, J=8.0 Hz, 1H), 6.06 (d, J=19.0 Hz, 1H), 5.63 (d, J=8.0 Hz, 1H), 3.94 (dd, J=12.0, 2.0 Hz, 1H), 3.87 (s, 1H), 3.73 (dd, J=12.0, 2.5 Hz, 1H), 1.29 (d, J=22.5 Hz, 3H).

Step 1-5

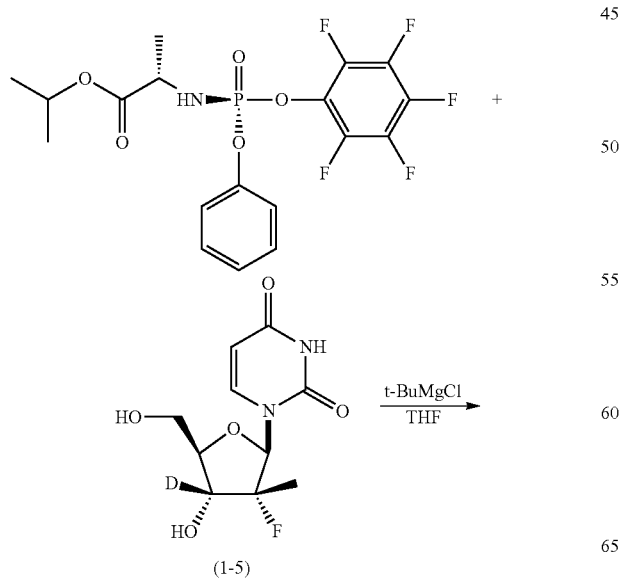

(1-5)

Example 2

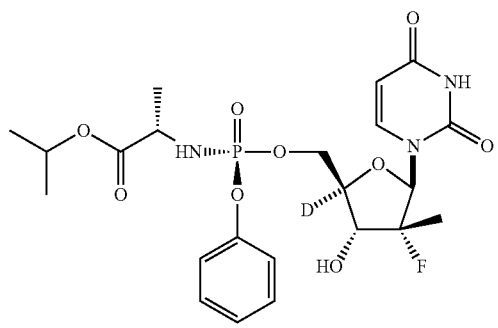 [SMILES: [2H][C@]1(CO[P@@](=O)(N[C@@H](C)C(=O)OC(C)C)Oc2ccccc2)O[C@@H](n2ccc(=O)[nH]c2=O)[C@](C)(F)[C@@H]1O]

Step 2-1

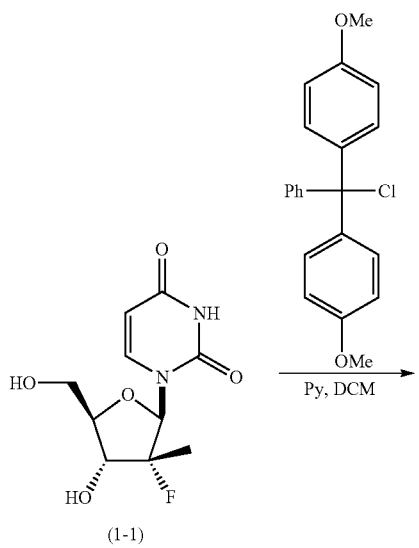

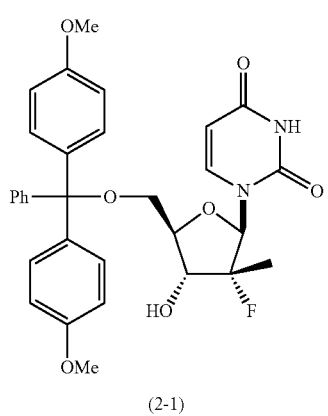

To a solution of compound (1-1) (1.289 g, 4.95 mmol in pyridine (6.52 mL, were added DCM (6.52 mL. The solution was cooled to 0° C. To the solution was added 4,4'-dimethoxytrityl chloride (1.846 g, 5.45 mmol.). The solution was stirred at 0° C. for 4 h. Methanol (0.6 mL) was added to quench the reaction. The solution was concentrated to dryness under reduced pressure and the residue was partitioned between EtOAc (65 mL) and water (7 mL). The organic solution was washed with brine (10 mL), dried over Na$_2$SO$_4$, filtered, and concentrated to give a crude compound (2-1)(3.41 g) which was used directly in next step. MS (ESI): m/e 585.25 (M+23).

Step 2-2

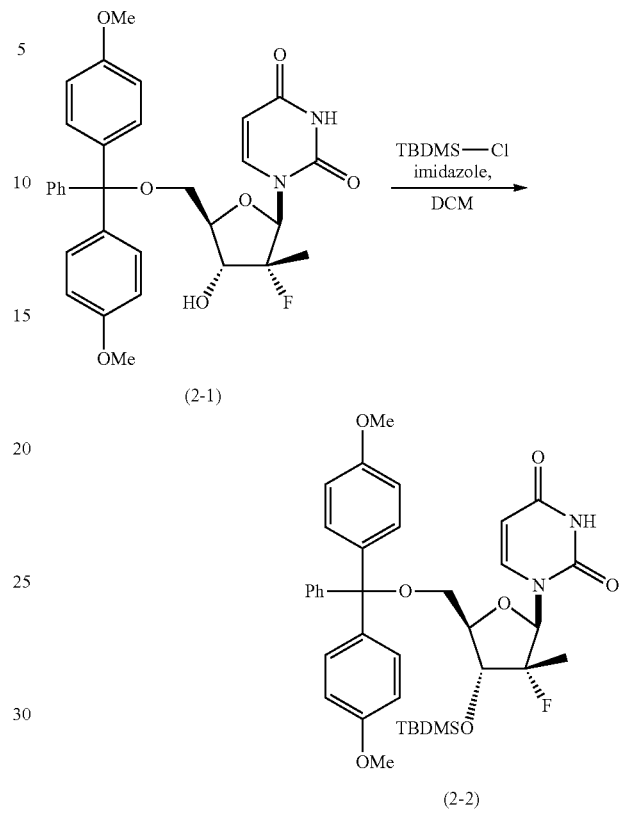

To the solution of compound (2-1)(3.41 g, 82% weight purity, 4.95 mmol.) in DCM (13.03 mL) at rt, were added imidazole (1.011 g, 14.85 mmol.) and t-butyldimethylsilyl chloride (1.119 g, 7.43 mmol.). The solution was stirred at room temperature for 24 h. Methanol (0.65 mL) was added to quench the reaction and the solvent was removed by rotovap and the residue was partitioned between ethyl acetate (60 mL) and water (8 mL). The organic solution was separated, washed by water (8 mL) and brine (6 mL), dried over Na$_2$SO$_4$, filtered, and concentrated to crude product. The crude product was purified by combiflash (silica gel, 2-40% EtOAc in Hexane) to give the compound (2-2) (3.2 g, 96% yield). MS (ESI): m/e 699.42 (M+23).

Step 2-3

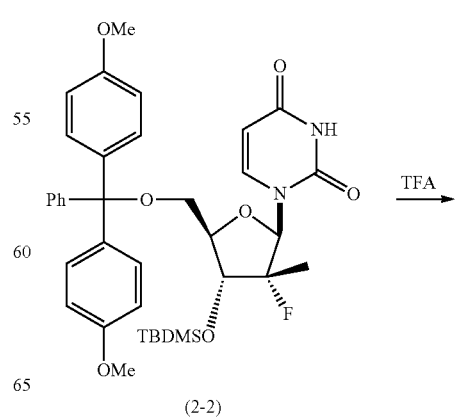

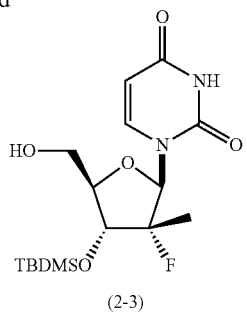

(2-3)

To a flask containing the compound (2-2) (3.2 g, 4.73 mmol.) at room temperature, was added the solvent of 1% TFA in dichloromethane (28 mL). The solution was stirred at room temperature for 1 h. Water (2.8 mL) was added and the solution was stirred at room temperature for 1 h. Methanol (1.4 mL) was slowly added and the mixture was stirred at room temperature for 1.5 h. Additional TFA (0.25 eq, 0.091 mL) was added. The mixture was stirred at room temperature for 45 min. 28% aqueous ammonium hydroxide was added to adjust the solution pH to 7. The mixture was diluted by DCM (60 mL) and water (10 mL). The organic layer was separated, dried over $Na_2SO_4$, filtered and concentrated to dryness. The crude product was purified by recrystallization in DCM/hexane to give the compound (2-3) (1.342 g, 76% yield). MS (ESI): m/e 375.20 (M+1), 397.19 (M+23).

Step 2-4

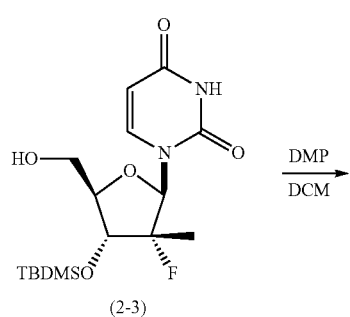

(2-3)

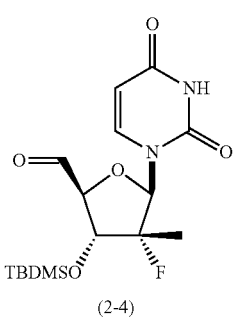

(2-4)

To a mixture of compound (2-3) (0.718 g, 1.917 mmol.) in DCM (13 mL) at 0° C., Dess-Martin periodinane (1.22 g, 2.88 mmol.) was added. The mixture was stirred at room temperature for 3 h. The mixture was treated with $Et_2O$ (15 mL), sat. $NaHCO_3$ (5 mL) and half-diluted sat. $Na_2S_2O_3$ (5 mL). The mixture was stirred at room temperature for 5 min. The mixture was further diluted by $Et_2O$ (20 mL). The organic layer was separated and aqueous layer was extracted by DCM (2×15 mL). The combined organic layers was filtered and concentrated to give a crude product. The crude product was purified by Combiflash (silica gel, 5%-100% EtOAc in Hexanes) to give aldehyde compound (2-4) (0.51 g, 71.4% yield). MS (ESI): m/e 373.07 (M+1), 395.05 (M+23).

Step 2-5

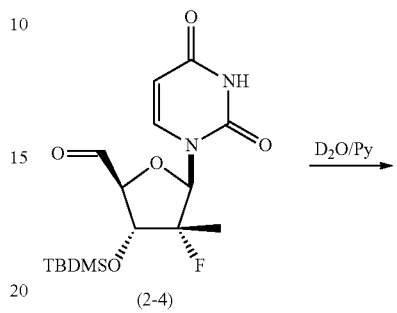

(2-4)

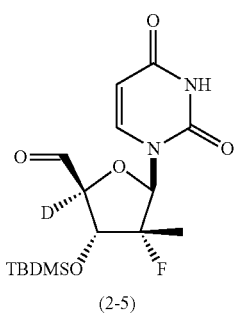

(2-5)

To a flask, was added aldehyde compound (2-4) (0.313 g, 0.840 mmol.) at room temperature, followed by addition of pyridine (16.79 mL, 208 mmol.) and $D_2O$ (4.48 mL, 224 mmol.). The solution was stirred at 50° C. for 28 h. The reaction was monitored by 1HNMR. Upon the completed reaction, solvent was removed via reduced pressure. The mixture was traced by $D_6$-acetone and $CDCl_3$ to remove remaining pyridine. Upon the solvent was removed, crude deuterated aldehyde was dried under vacuum to give light brown solid compound (2-5) (0.380 g), which was directly used in next step. MS (ESI): m/e 374.20 (M+1), 396.18 (M+23).

Step 2-6

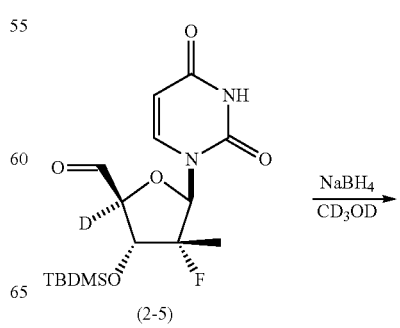

(2-5)

-continued

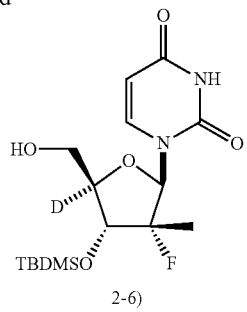

(2-6)

Step 2-8

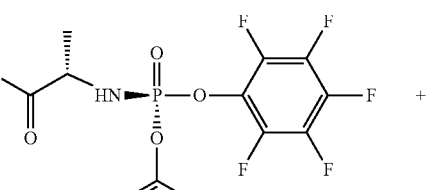

+

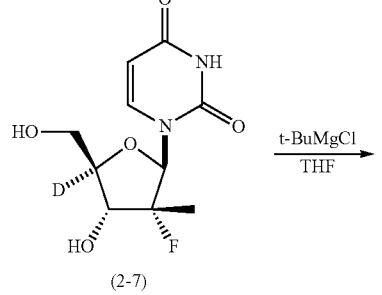

To a solution of crude deuterated aldehyde compound (2-5) (0.127 g, 83% weight purity, 0.283 mmol.) in MeOH-D$_4$(2.83 mL) at 0° C., was added NaBH$_4$ (0.032 g, 0.849 mmol.). The mixture was stirred at room temperature for 30 min. the reaction was monitored by TLC. Upon repeating the same sequence three more times (1 eq. NaBH$_4$ (10.71 mg, 0.283 mmol.) for each, TLC indicated that the reaction is completed. The solvent was removed. The mixture was partioned between EtOAc and Sat. NH$_4$Cl. The organic layer was separated and washed by brine, dried over Na$_2$SO$_4$, filtered, concentrated to give the deuterated alcohol compound (2-6) (0.88 g, 83% yield). MS (ESI): m/e 398.12 (M+23).

Step 2-7

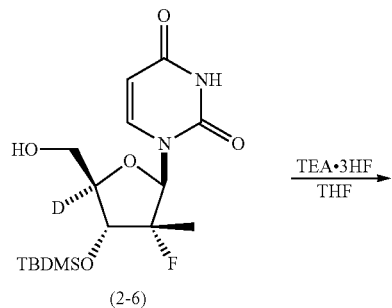

(2-6)

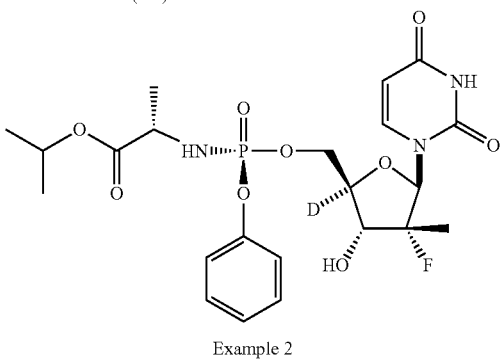

Example 2

The example 2 was prepared by using same procedure used in the preparation of example 1. The compound of example 2 was obtained with 64% yield. MS (ESI): m/e 531.19 (M+1), 553.16 (M+23); $^1$H NMR (500 MHz, CDCl$_3$) δ 8.48 (s, 1H), 7.44 (d, J=8.0 Hz, 1H), 7.35-7.17 (m, 5H), 6.16 (d, J=18.0 Hz, 1H), 5.68 (d, J=8.0 Hz, 1H), 5.03-4.98 (m, 1H), 4.54-4.50 (m, 1H), 4.44-4.40 (m, 1H), 3.96-3.88 (m, 2H), 3.85-3.81 (m, 1H), 3.55 (s, 1H), 1.39 (d, J=22.5 Hz, 3H), 1.34 (d, J=7.0 Hz, 3H), 1.22 (d, J=6.5 Hz, 6H).

Example 3

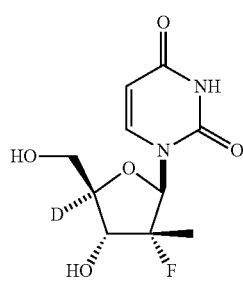

(2-7)

To a solution of deuterated alcohol compound (2-6) (0.044 g, 0.117 mmol.) in THF (2.344 mL) at room temperature, was added triethylamine tris-hydrofluoride (0.153 mL, 0.937 mmol.). The mixture was stirred at room temperature for 36 h. The reaction was quenched by ethoxytrimethylsilane (0.439 mL, 2.81 mmol.). The mixture was stirred at room temperature for 10 min. The solvent was removed and the mixture was purified by combiflash (silica gel, 0-7% MeOH in DCM) to give the compound (2-7) (0.02 g, 65.3% yield) as a white solid. MS (ESI): m/e 284.09 (M+23).

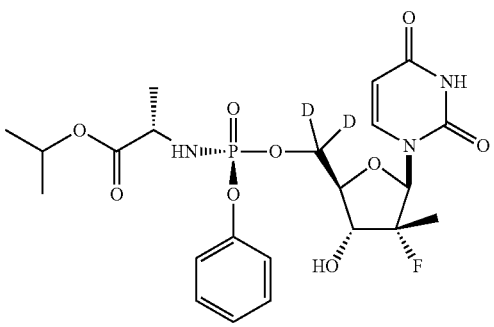 [SMILES: [2H]C([2H])(O[P@@](=O)(N[C@@H](C)C(=O)OC(C)C)Oc1ccccc1)[C@H]1O[C@@H](n2ccc(=O)[nH]c2=O)[C@](C)(F)[C@@H]1O]

Step 3-1

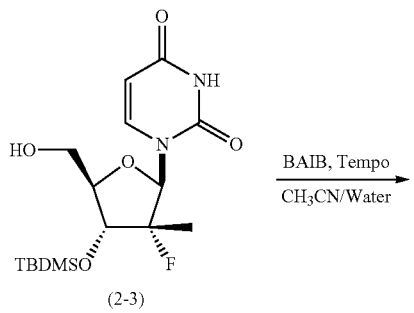

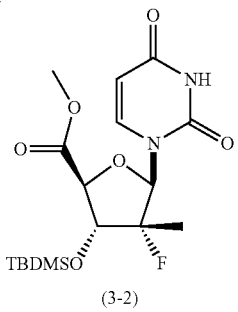

To the solution of compound (2-3) (0.25 g, 0.668 mmol.) in acetonitrile (2.88 mL), was added bis-(acetoxy)iodo benzene (0.516 g, 1.602 mmol.), TEMPO (0.029 g, 0.184 mmol.) and water (2.88 mL). The mixture was stirred at room temperature for 3 hours and gradually poured into 0.5 M KOH (23 mL). After stirring for 10 minutes at rt, the mixture was extracted with EtOAc (40 mL). EtOAc layers were washed with water (40 mL). The combined aqueous layers was acidified carefully under cooling to pH=2 with 2 M aqueous HCl. The resulted slurry was extracted by EtOAc (2×75 mL). The EtOAc extraction was washed by brine, dried over $Na_2SO_4$, filtered, concentrated to give acid compound (3-1) (0.241 g, 93% yield). MS (ESI): m/e 389.17 (M+1), 411.15 (M+23).

Step 3-2

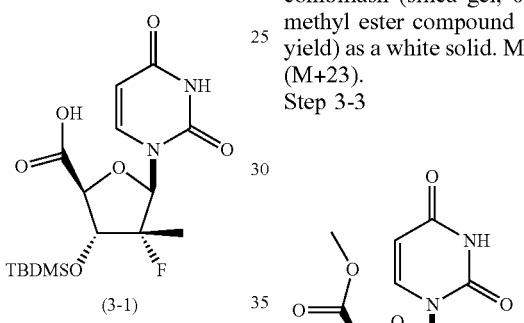

To a solution of acid compound (3-1) (0.101 g, 0.260 mmol.) in benzene (3.47 mL) and MeOH (2.78 mL), was added trimethylsilyldiazomethane in hexane (2M) dropwise until mild yellow color did not disappear after stirring for 1 minute (totally trimethylsilyldiazomethane (0.936 mmol., 3.6 eq) was added). Then, the reaction was immediately quenched by acetic acid (0.119 mL, 2.080 mmol.). The solvent was removed. The crude product was purified by combiflash (silica gel, 0-60% EtOAc in Hexanes) to give methyl ester compound (3-2) (0.103 g, 0.256 mmol., 98% yield) as a white solid. MS (ESI): m/e 425.37 (M+1), 447.37 (M+23).

Step 3-3

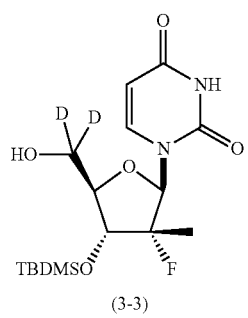

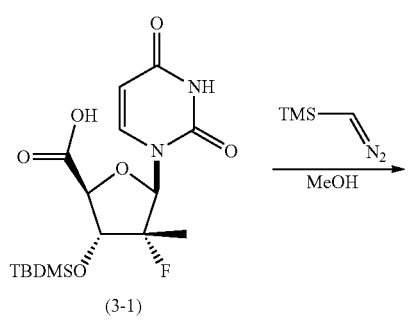

To a solution of methyl ester compound (3-2) (0.025 g, 0.062 mmol.) in MeOH (0.259 mL) and t-BuOH (1.294 mL) at 0° C., Sodium borodeuteride (10.40 mg, 0.248 mmol.) was added. The mixture was stirred at room temperature for 1 h. Then additional sodium borodeuteride (10.40 mg, 0.248 mmol.) was added at 0° C. The mixture was stirred at room temperature for 3 h. The reaction mixture was treated with MeOH (0.1 mL), and then diluted with EtOAc (20 mL). The mixture was treated with 0.5M aqueous HCl until no bubble was observed. The pH of the mixture was adjusted to 8 by addition of sat. $NaHCO_3$. The organic layer was separated. The aqueous layer was extracted by EtOAc. The combined organic layers was washed by brine, dried over $Na_2SO_4$, filtered, concentrated to give a crude 5'-D₂-alcohol compound (3-3) (27 mg) which was used directly for next step. MS (ESI): m/e 399.25 (M+23).

Step 3-4

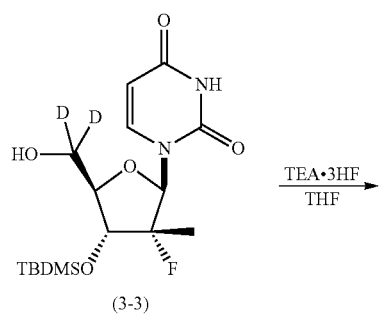

(3-3)

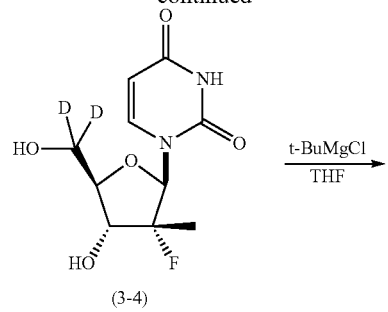

(3-4)

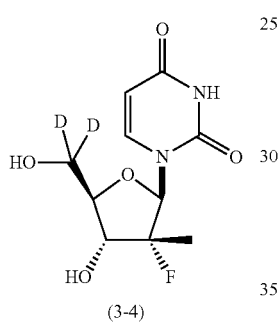

(3-4)

To a solution of 5'-D₂-alcohol compound (3-3) (0.027 g, 88% weight purity, 0.062 mmol.) in THF (1.240 mL) at rt, was added triethylamine tris-hydrofluoride (0.081 mL, 0.496 mmol., 8 eq). The mixture was stirred at room temperature for 20 h. The second portion of triethylamine tris-hydrofluoride (2 eq) was added at room temperature. The mixture was stirred at room temperature for 8 h. The 3rd portion of triethylamine tris-hydrofluoride (4 eq) was added at room temperature. The mixture was stirred at room temperature for 16 h. The mixture was concentrated and purified by two flash chromatography (1st: silica gel, 0-7% MeOH in DCM; 2nd: silica gel, 0-5% MeOH in DCM) to give compound (3-4) (0.011 g, 0.042 mmol., 67.7% yield).

Step 3-5

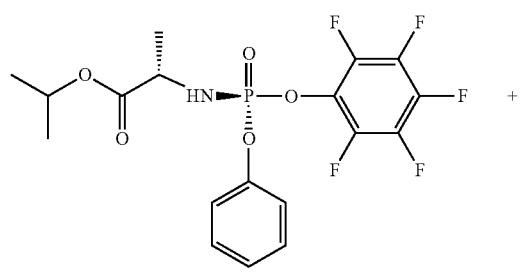

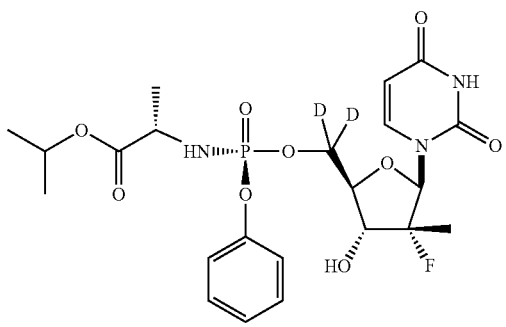

example 3

To a solution of compound (3-4) (0.015 g, 0.057 mmol.) in THF (0.318 mL) at 0° C., was added tert-butylmagnesium chloride (1M, in THF) (0.120 mL, 0.120 mmol.) dropwise. The resulted slurry was stirred at 0° C. for 15 min and room temperature for 15 min. The mixture was cooled down to 0° C. A solution of (S)-2-[(S)-(2,3,4,5,6-pentafluorophenoxy)-phenoxyphosphorylamino]propionic acid iso-propyl ester (0.047 g, 0.103 mmol.) in THF (0.3 mL) was added into the slurry. The mixture was stirred at 0° C. to room temperature for 16 h. The reaction was quenched by addition of sat. NaHCO₃ (2 mL) and diluted by EtOAc(15 mL) and Water (2 mL). The organic layer was separated; the aqueous layer was extracted by EtOAc (10 mL). The combined organic layers were washed by brine, dried over Na₂SO₄, filtered, concentrated to give a crude product. The crude product was purified by prep-HPLC to give the title compound of example 3 (0.025 g, 82% yield). MS (ESI): m/e 532.26 (M+1), 554.24 (M+23); $^1$H NMR (500 MHz, CDCl₃) δ 7.99 (s, 1H), 7.44 (d, J=8.0 Hz, 1H), 7.36-7.17 (m, 5H), 6.16 (d, J=18.0 Hz, 1H), 5.69 (dd, J=8.0, 2.0 Hz, 1H), 5.03-4.98 (m, 1H), 4.10 (d, J=11.0 Hz, 1H), 3.94-3.88 (m, 2H), 3.66-3.62 (m, 1H), 3.36-3.35 (m, 1H), 1.41 (d, J=22.0 Hz, 3H), 1.34 (d, J=6.5 Hz, 3H), 1.23 (dd, J=6.5, 2.0 Hz, 6H).

Example 4

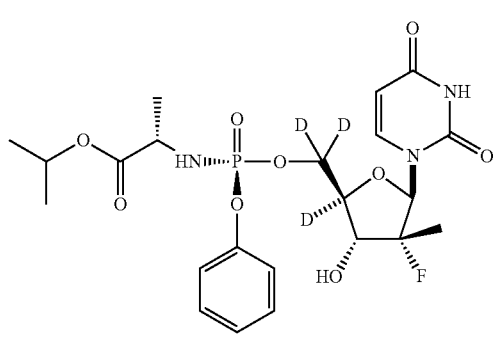 [SMILES: [2H]C([2H])(O[P@@](=O)(N[C@@H](C)C(=O)OC(C)C)Oc1ccccc1)[C@@]1([2H])O[C@@H](n2ccc(=O)[nH]c2=O)[C@](C)(F)[C@@H]1O]

Step 4-1

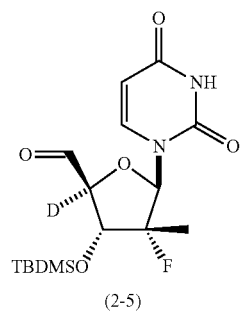

To a mixture of deuterated aldehyde compound (2-5) (0.215 g, 0.576 mmol.), sodium phosphate monobasic (0.069 g, 0.576 mmol.), and 2-methyl-2-butene (2M, in THF) (1.267 mL, 2.53 mmol.) in t-BuOD (3.93 mL) and $D_2O$ (1.308 mL), was added sodium chlorite (0.286 g, 3.17 mmol.). The mixture was stirred at room temperature for 5 h. The reaction mixture was treated with 0.5M KOH (10 mL) and EtOAc (25 mL×2), the organic layer was separated and extracted by 0.5M KOH (10 mL). The combined aqueous layers was acidified to pH=2 by addition of 2M aqueous HCl. The resulted slurry was extracted with EtOAc (25 mL×2), The combined EtOAc solution was dried over $Na_2SO_4$, filtered, concentrate, and dried under vacuum to give the crude deuterated acid compound (4-1) (0.205 g, 91% yield) which was used directly for next step. $^1$H NMR (500 MHz, $CD_3OD$) δ 8.02 (d, J=8.0 Hz, 1H), 6.07 (d, J=16.5 Hz, 1H), 5.65 (d, J=8.0 Hz, 1H), 4.10 (d, J=18.5 Hz, 1H), 1.24 (d, J=22.5 Hz, 3H), 0.81 (s, 9H), 0.02 (s, 3H), 0.01 (s, 3H).

Step 4-2

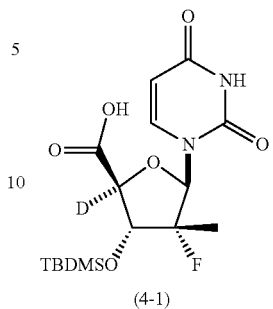

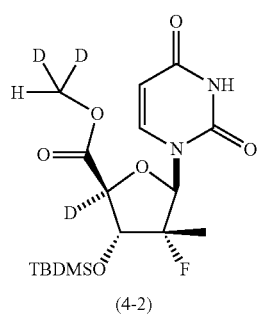

To a solution of acid compound (4-1) (0.205 g, 0.526 mmol.) in benzene (7.03 mL) and $CD_3OD$ (5.62 mL), was added trimethylsilyldiazomethane in hexane (2M) dropwise until mild yellow color did not disappear after stirring for 0.5 minute (totally trimethylsilyldiazomethane in hexane (2M) (0.855 mL, 1.711 mmol.) was added). Then, the reaction was immediately quenched by addition of $CD_3COOD$ (0.257 mL, 4.21 mmol.). The solvent was removed. The residue was dried under vacuum to give the crude deuterated ester compound (4-2) (0.205 g, 96% yield) as a white solid which was used directly for next step. MS (ESI): m/e 428.37 (M+23).

Step 4-3

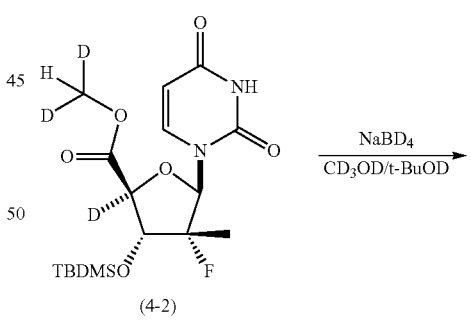

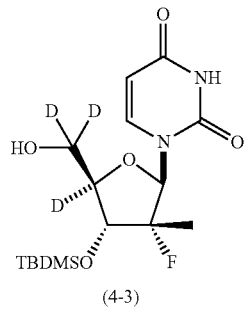

To a solution of ester compound (4-2) (0.107 g, 0.264 mmol.) in CD₃OD (0.440 mL) and t-BuOD (2.199 mL) at 0° C. sodium borodeuteride (0.044 g, 1.055 mmol.) was added. The mixture was stirred at room temperature for 3 h. The reaction mixture was treated with CD₃OD (0.4 mL), and then diluted with EtOAc. The mixture was treated with 0.5M aqueous HCl until no bubble was observed. The PH of the mixture was adjusted to 8 by addition of sat. NaHCO₃. The organic layer was separated. The aqueous layer was extracted by EtOAc. The combined organic layers was washed by brine, dried over Na₂SO₄, filtered, concentrated to give a crude 3',5'-D₃ nucleoside compound (4-3) (88 mg, 88% yield) which was used directly for next step. ¹H NMR (500 MHz, CDCl₃) δ 9.01 (s, 1H), 7.84 (d, J=7.5 Hz, 1H), 6.09 (d, J=18.0 Hz, 1H), 5.73 (d, J=7.5 Hz, 1H), 4.11-4.06 (m, 2H), 1.33 (d, J=21.5 Hz, 1H), 0.91 (s, 9H), 0.13 (s, 3H), 0.12 (s, 3H).

Step 4-4

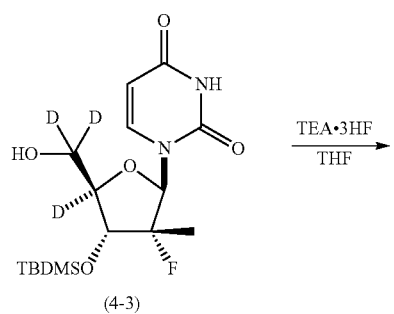

To a solution of compound (4-3) (0.088 g, 0.233 mmol.) in THF (4.66 mL) at room temperature, was added triethylamine tris-hydrofluoride (0.380 mL, 2.331 mmol.). The mixture was stirred at room temperature for 36 h. The reaction was quenched by ethoxytrimethylsilane (1.092 mL, 6.99 mmol.). The mixture was stirred at room temperature for 10 min. The solvent was removed. The mixture was purified by combiflash (silica gel, 0-7% MeOH in DCM) to give compound (4-4) (0.029 g, 47.3% yield) as a white solid. ¹H NMR (500 MHz, CD₃OD) δ 7.92 (d, J=8.0 Hz, 1H), 5.96 (d, J=18.5 Hz, 1H), 5.54 (d, J=8.0 Hz, 1H), 3.80 (d, J=23.5 Hz, 1H), 1.19 (d, J=21.5 Hz, 3H).

Step 4-5

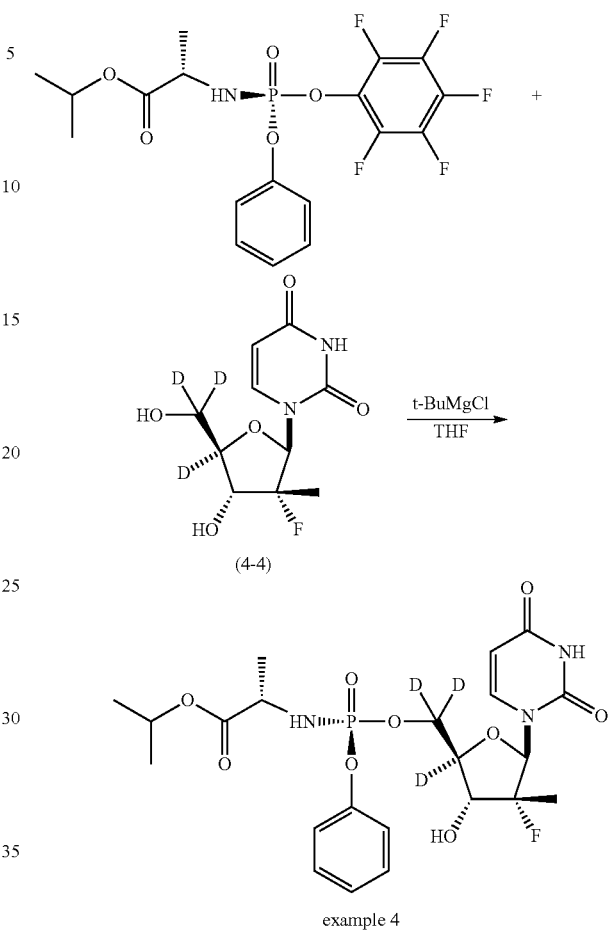

example 4

The procedure of phosphoamidate prodrug formation was used for preparation of example 4 is same as the procedure used in preparation of example 1. The product was obtained with 69% yield. MS (ESI): m/e 533.26 (M+1), 555.23 (M+23). ¹H NMR (500 MHz, CDCl₃) δ 8.05 (s, 1H), 7.44 (d, J=8.0 Hz, 1H), 7.36-7.17 (m, 5H), 6.16 (d, J=18.5 Hz, 1H), 5.69 (d, J=8.0 Hz, 1H), 5.03-4.97 (m, 1H), 3.96-3.88 (m, 2H), 3.68-3.64 (m, 1H), 3.37-3.36 (m, 1H), 1.41 (d, J=22.5 Hz, 3H), 1.34 (d, J=6.5 Hz, 3H), 1.23 (dd, J=6.5, 1.5 Hz, 6H).

Biological Activity

1. HCV Replicon Cell Lines

HCV replicon cell lines (kindly provided by R. Bartenschlager) isolated from colonies as described by Lohman et al. (Lohman et al. (1999) Science 285: 110-113, expressly incorporated by reference in its entirety) and used for all experiments. One of the HCV replicon cell lines (strain Conl, genotype 1b) has the nucleic acid sequence set forth in EMBL Accession No.: AJ242651, the coding sequence of which is from nucleotides 1801 to 8406. Another replicon cell line (strain H77, genotype 1a) was constructed as described by Yi et al. (Yi et al. (2004) Journal of Virology 78(15):7904-15). The coding sequences of the published HCV replicons were synthesized and subsequently assembled in plasmids using standard molecular biology techniques.

One replicon cell line ("SGR 11-7") stably expresses HCV replicon RNA, genotype 1b, which consists of (i) the HCV 5'UTR fused to the first 12 amino acids of the capsid protein, (ii) the neomycin phosphotransferase gene (neo), (iii) the IRES from encephalomyocarditis virus (EMCV), and (iv) HCV NS2 to NS5B genes and the HCV 3'UTR. Another replicon cell line ("Huh-1a7") described by Yi et al. (Yi et al. (2004) Journal of Virology 78(15):7904-15, expressly incorporated by reference in its entirety) stably expresses HCV replicon RNA, genotype 1a, which consists of (i) the HCV 5'UTR fused to the first 12 amino acids of the capsid protein, (ii) the HIV tat protein, (iii) the neomycin phosphotransferase gene (neo), (iv) the IRES from encephalomyocarditis virus (EMCV), and (v) HCV NS3 to NS5B genes that harbor cell culture adaptive mutations (Q1067R, K1691R, S2204I) and the HCV 3'UTR.

These cell lines are maintained at 37° C., 5% $CO_2$, 100% relative humidity in DMEM (Cat#11965-084, Invitrogen), with 10% fetal calf serum ("FCS", Invitrogen), 1% non-essential amino acids (Invitrogen), 1% of Glutamax (Invitrogen), 1% of 100× penicillin/streptomycin (Cat#15140-122, Invitrogen) and Geneticin (Cat#10131-027, Invitrogen) at 0.75 mg/mL or 0.25 mg/mL for 11-7 and Huh-1a7 cells, respectively.

2. HCV Replicon Assay—qRT-PCR $EC_{50}$ values of single agent compounds were determined by HCV RNA detection using quantitative RT-PCR, according to the manufacturer's instructions, with a TAQMAN® One-Step RT-PCR Master Mix Reagents Kit (Cat# AB 4309169, Applied Biosystems) on an ABI Model 7500 thermocycler. $EC_{50}$ values of combinations are similarly determined by HCV RNA detection using quantitative RT-PCR. The TAQMAN primers to use for detecting and quantifying HCV RNA obtained from Integrated DNA Technologies. HCV RNA is normalized to GAPDH RNA levels in drug-treated cells, which is detected and quantified using the Human GAPDH Endogenous Control Mix (Applied Biosystems, AB 4310884E). Total cellular RNA is purified from 96-well plates using the RNAqueous 96 kit (Ambion, Cat# AM1812). Chemical agent cytotoxicity is evaluated using an MTS assay according to the manufacturer's directions (Promega).

The compounds of the present invention can be effective against the HCV 1a and 1b genotypes. It should also be understood that the compounds of the present invention can inhibit multiple genotypes of HCV. In one embodiment, compounds of the present invention are active against the 1a, 1b, 2a, 2b, 3a, 4a, and 5a genotypes. Table 5 shows the $EC_{50}$ values of representative compounds of the present invention against the HCV 1a and 1b genotypes from the above described qRT-PCR. $EC_{50}$ ranges against HCV 1a are as follows: A>1 µM; B 0.1-1 µM; C<0.1 µM.

TABLE 5

| Genotype-1a replicon $EC_{50}$ | |
|---|---|
| Example | 1a $EC_{50}$ |
| 1 | B |
| 2 | B |
| 3 | B |
| 4 | B |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of Formula I or a pharmaceutically acceptable salt, ester, stereoisomer, tautomer, solvate, or combination thereof:

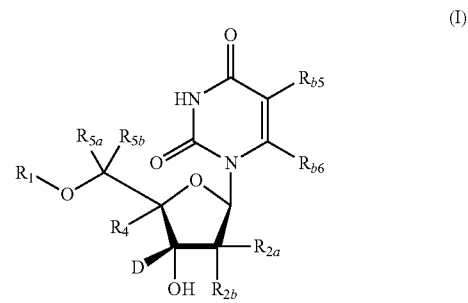

wherein:
D is deuterium;
$R_1$ is

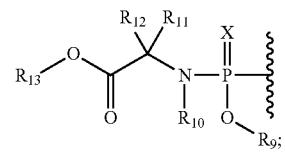

where X is O or S; $R_9$ is $R_7$ wherein $R_7$ is selected from the group consisting of: substituted or unsubstituted —$C_1$-$C_8$ alkyl, substituted or unsubstituted —$C_2$-$C_8$ alkenyl, substituted or unsubstituted —$C_2$-$C_8$ alkynyl, substituted or unsubstituted aryl, substituted or unsubstituted heteroaryl, and substituted or unsubstituted heterocyclic; $R_{10}$, $R_{11}$ and $R_{12}$ are each independently selected from the group consisting of: a) hydrogen; b) unsubstituted or substituted —$C_1$-$C_8$ alkyl; c) $R_{11}$ is hydrogen, $R_{12}$ and $R_{10}$ taken together with the intervening carbon and nitrogen atoms form a heterocyclic ring; d) $R_{11}$ and $R_{12}$ taken together with the carbon atom to which they are attached form a ring; and $R_{13}$ is hydrogen or $R_7$;

$R_{2a}$ is selected from the group consisting of:
1) Hydrogen;
2) Deuterium;
3) Halogen;
4) Nitrile;
5) Substituted or unsubstituted —$C_1$-$C_8$ alkyl;
6) Substituted or unsubstituted —$C_2$-$C_8$ alkenyl; and
7) Substituted or unsubstituted —$C_2$-$C_8$ alkynyl;

$R_{2b}$ is independently selected from the group consisting of:
1) Halogen; and
2) $OR_9$;

$R_9$ at each occurrence is selected from the group consisting of: hydrogen, hydroxy protecting group, $R_{10b}$, —C(O)$R_{10b}$, —C(O)O$R_{10b}$, and —C(O)N$R_{11a}$$R_{11b}$; wherein $R_{10b}$ at each occurrence is independently selected from the group consisting of: substituted or unsubstituted —$C_1$-$C_8$ alkyl, substituted or unsubstituted —$C_2$-$C_8$ alkenyl, substituted or unsubstituted —$C_2$-$C_8$ alkynyl, substituted or unsubstituted aryl, substituted or unsubstituted heteroaryl, and substituted or unsubstituted heterocyclic; $R_{11a}$ and $R_{11b}$ at each occurrence are each independently selected from the group consisting of: hydrogen and $R_{10b}$; or alternatively $R_{11a}$ and $R_{11b}$ taken together with the nitrogen atom to which they are attached form a heterocyclic ring;

or $R_{2a}$ and $R_{2b}$ taken together with the carbon atom to which they are attached form a 3-to 6-membered cycloalkyl ring or a 3- to 6-membered heterrocycloalkyl ring containing one hereroatom selected from N, O, and S, each of which is optionally substituted;

$R_4$ is hydrogen, deuterium, $N_3$, halogen or optionally substituted methyl;

$R_{5a}$ and $R_{5b}$ are each independently selected from the group consisting of:
1) Hydrogen;
2) Deuterium;
3) Substituted or unsubstituted —$C_1$-$C_8$ alkyl;
4) Substituted or unsubstituted —$C_2$-$C_8$ alkenyl; and
5) Substituted or unsubstituted —$C_2$-$C_8$ alkynyl;
or $R_{5a}$ and $R_{5b}$ are taken together with the carbon atom to which they are attached to form a group selected from —$C_3$-$C_8$ cycloalkyl, —$C_3$-$C_8$ cycloalkenyl, or —$C_3$-$C_8$ cycloalkynyl; and $R_{b5}$ and $R_{b6}$ are each independently selected from the group consisting of:
1) Hydrogen; and
2) Deuterium.

2. The compound of claim 1, wherein said compound is of Formula II, or a pharmaceutically acceptable salt, ester, stereoisomer, tautomer, solvate, or combination thereof:

(II)

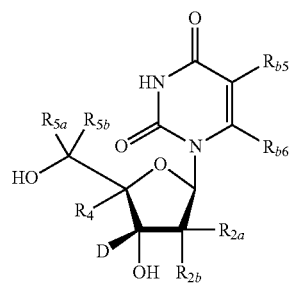

wherein, $R_{2a}$, $R_{2b}$, $R_4$, R, $R_{b5}$, $R_{b6}$, $R_{5a}$ and $R_{5b}$ are as defined in claim 1.

3. The compound of claim 1, wherein said compound is of Formula IV, or a pharmaceutically acceptable salt, ester, stereoisomer, tautomer, solvate, or combination thereof:

(III)

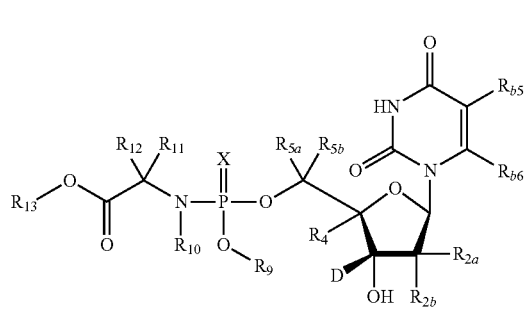

wherein, X, $R_{2a}$, $R_{2b}$, $R_{b5}$, $R_{b6}$, $R_4$, $R_{5a}$, $R_{5b}$, $R_9$, Rio, $R_{11}$, $R_{12}$, and $R_{13}$ are as defined in claim 1.

4. A compound selected from:

(a) compounds of Formula III-1 wherein, $R_{2a}$, $R_{2b}$, $R_{b5}$, and $R_{b6}$ are delineated for each compound in Table 1:

(III-1)

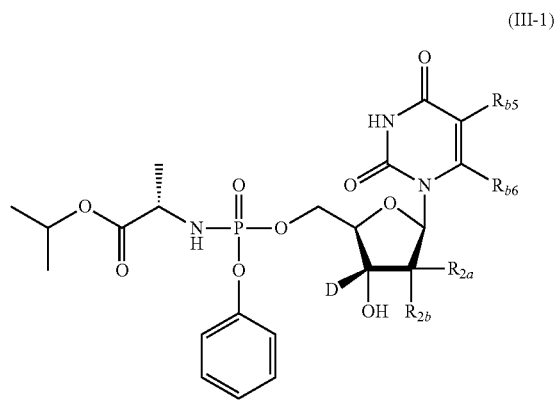

TABLE 1

| Example | $R_{2a}$ | $R_{2b}$ | $R_{b5}$ | $R_{b6}$ | Example | $R_{2a}$ and $R_{2b}$ | $R_{b5}$ | $R_{b6}$ |
|---|---|---|---|---|---|---|---|---|
| 1 | Me | OH | D | H | 11 | cyclopropyl | D | H |
| 2 | Me | OH | D | D | 12 | cyclopropyl | D | D |
| 3 | Me | OH | CD₃ | H | 13 | cyclopropyl | CD₃ | H |
| 4 | Me | OH | CD₃ | D | 14 | cyclopropyl | CD₃ | D |
| 5 | Me | OH | H | H | 15 | cyclopropyl | H | H |
| 6 | Me | F | D | H | 16 | oxetanyl | D | H |
| 7 | Me | F | D | D | 17 | oxetanyl | D | D |
| 8 | Me | F | CD₃ | H | 18 | oxetanyl | CD₃ | H |

TABLE 1-continued

| Example | $R_{2a}$ | $R_{2b}$ | $R_{b5}$ | $R_{b6}$ | Example | $R_{2a}$ and $R_{2b}$ | $R_{b5}$ | $R_{b6}$ |
|---|---|---|---|---|---|---|---|---|
| 9 | Me | F | $CD_3$ | D | 19 | | $CD_3$ | D |
| 10 | Me | F | H | H | 20 | | H | H |

(b) Compounds according to Formula III-2, wherein, $R_{2a}$, $R_{2b}$, $R_{b5}$, and $R_{b6}$ are delineated for each compound in Table 2:

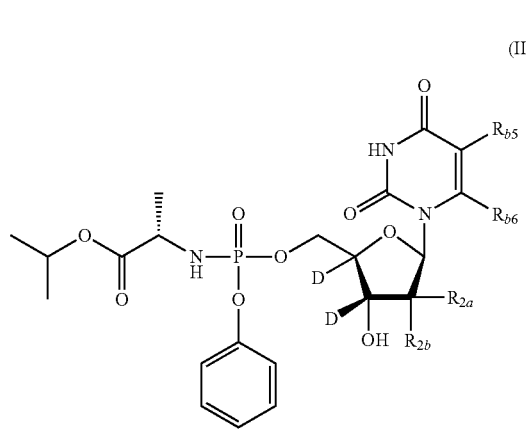

(III-2)

TABLE 2

| Example | $R_{2a}$ | $R_{2b}$ | $R_{b5}$ | $R_{b6}$ | Example | $R_{2a}$ and $R_{2b}$ | $R_{b5}$ | $R_{b6}$ |
|---|---|---|---|---|---|---|---|---|
| 21 | Me | OH | D | H | 31 | cyclopropyl | D | H |
| 22 | Me | OH | D | D | 32 | cyclopropyl | D | D |
| 23 | Me | OH | $CD_3$ | H | 33 | cyclopropyl | $CD_3$ | H |
| 24 | Me | OH | $CD_3$ | D | 34 | cyclopropyl | $CD_3$ | D |
| 25 | Me | OH | H | H | 35 | cyclopropyl | H | H |
| 26 | Me | F | D | H | 36 | oxetanyl | D | H |
| 27 | Me | F | D | D | 37 | oxetanyl | D | D |
| 28 | Me | F | $CD_3$ | H | 38 | oxetanyl | $CD_3$ | H |
| 29 | Me | F | $CD_3$ | D | 39 | oxetanyl | $CD_3$ | D |
| 30 | Me | F | H | H | 40 | oxetanyl | H | H |

(c) Compounds according to Formula III-3, wherein, $R_{2a}$, $R_{2b}$, $R_{b5}$ and $R_{b6}$ are delineated for each compound in Table 3:

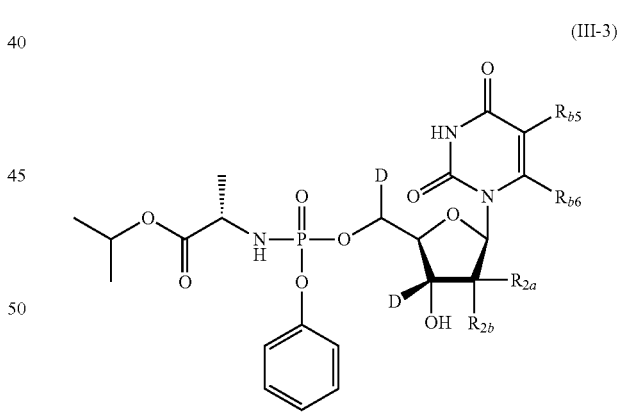

(III-3)

TABLE 3

| Example | R2a | R2b | Rb5 | Rb6 | Example | R2a and R2b | Rb5 | Rb6 |
|---|---|---|---|---|---|---|---|---|
| 41 | Me | OH | D | H | 51 | cyclopropyl | D | H |

TABLE 3-continued

| Example | R2a | R2b | Rb5 | Rb6 | Example | R2a and R2b | Rb5 | Rb6 |
|---|---|---|---|---|---|---|---|---|
| 42 | Me | OH | D | D | 52 | (1,1-cyclopropyl) | D | D |
| 43 | Me | OH | CD3 | H | 53 | (1,1-cyclopropyl) | CD3 | H |
| 44 | Me | OH | CD3 | D | 54 | (1,1-cyclopropyl) | CD3 | D |
| 45 | Me | OH | H | H | 55 | (1,1-cyclopropyl) | H | H |
| 46 | Me | F | D | H | 56 | (3,3-oxetanyl) | D | H |
| 47 | Me | F | D | D | 57 | (3,3-oxetanyl) | D | D |
| 48 | Me | F | CD3 | H | 58 | (3,3-oxetanyl) | CD3 | H |
| 49 | Me | F | CD3 | D | 59 | (3,3-oxetanyl) | CD3 | D |
| 50 | Me | F | H | H | 60 | (3,3-oxetanyl) ; | H | H |

(d) Compounds according to Formula III-4, wherein, $R_{2a}$, $R_{2b}$, $R_{b5}$ and $R_{b6}$ are delineated for each example in Table 4:

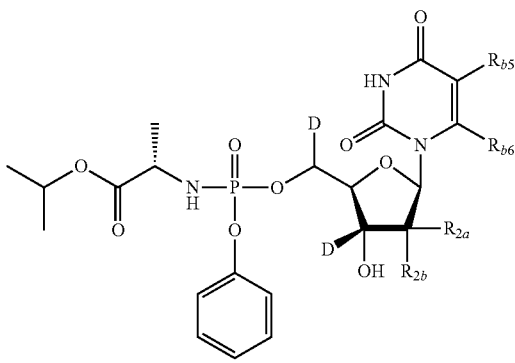

(III-4)

TABLE 4

| Example | $R_{2a}$ | $R_{2b}$ | $R_{b5}$ | $R_{b6}$ | Example | $R_{2a}$ and $R_{2b}$ | $R_{b5}$ | $R_{b6}$ |
|---|---|---|---|---|---|---|---|---|
| 61 | Me | OH | D | H | 71 | (1,1-cyclopropyl) | D | H |
| 62 | Me | OH | D | D | 72 | (1,1-cyclopropyl) | D | D |
| 63 | Me | OH | CD3 | H | 73 | (1,1-cyclopropyl) | CD3 | H |
| 64 | Me | OH | CD3 | D | 74 | (1,1-cyclopropyl) | CD3 | D |
| 65 | Me | OH | H | H | 75 | (1,1-cyclopropyl) | H | H |
| 66 | Me | F | D | H | 76 | (3,3-oxetanyl) | D | H |
| 67 | Me | F | D | D | 77 | (3,3-oxetanyl) | D | D |
| 68 | Me | F | CD3 | H | 78 | (3,3-oxetanyl) | CD3 | H |

TABLE 4-continued

| Example | $R_{2a}$ | $R_{2b}$ | $R_{b5}$ | $R_{b6}$ | Example | $R_{2a}$ and $R_{2b}$ | $R_{b5}$ | $R_{b6}$ |
|---|---|---|---|---|---|---|---|---|
| 69 | Me | F | $CD_3$ | D | 79 | 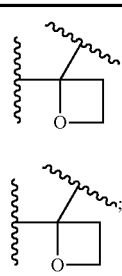 | $CD_3$ | D |
| 70 | Me | F | H | H | 80 | 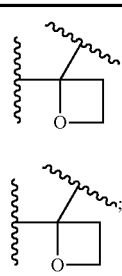 | H | H; |

(e) Compounds according to Formula III-5, wherein, $R_{2a}$, $R_{2b}$, $R_{b5}$ and $R_{b6}$ are delineated for each compound in Table 5:

(III-5)

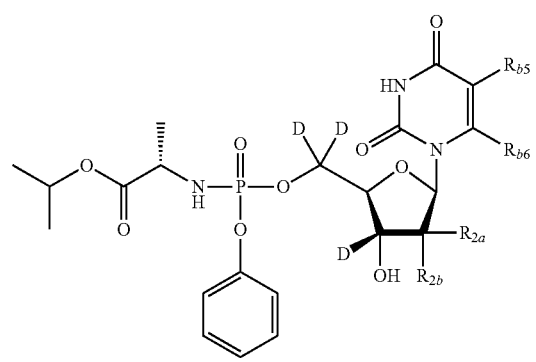

TABLE 5

| Example | $R_{2a}$ | $R_{2b}$ | $R_{b5}$ | $R_{b6}$ | Example | $R_{2a}$ and $R_{2b}$ | $R_{b5}$ | $R_{b6}$ |
|---|---|---|---|---|---|---|---|---|
| 81 | Me | OH | D | H | 91 | | D | H |
| 82 | Me | OH | D | D | 92 | | D | D |
| 83 | Me | OH | $CD_3$ | H | 93 | | $CD_3$ | H |
| 84 | Me | OH | $CD_3$ | D | 94 | | $CD_3$ | D |
| 85 | Me | OH | H | H | 95 | | H | H |
| 86 | Me | F | D | H | 96 | | D | H |
| 87 | Me | F | D | D | 97 | | D | D |
| 88 | Me | F | $CD_3$ | H | 98 | | $CD_3$ | H |
| 89 | Me | F | $CD_3$ | D | 99 | | $CD_3$ | D |
| 90 | Me | F | H | H | 100 | | H | H; |

(f) Compounds according to Formula III-6, wherein $R_{2a}$, $R_{2b}$, $R_{b5}$ and $R_{b6}$ are delineated for each example in Table 6:

(III-6)

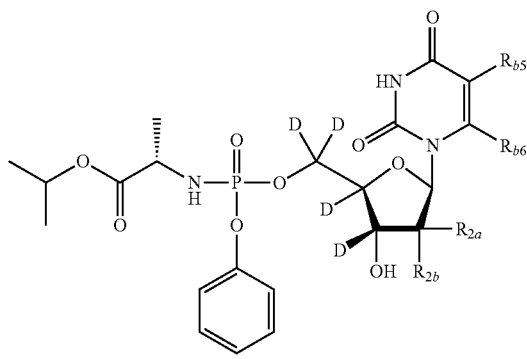

TABLE 6

| Example | $R_{2a}$ | $R_{2b}$ | $R_{b5}$ | $R_{b6}$ | Example | $R_{2a}$ and $R_{2b}$ | $R_{b5}$ | $R_{b6}$ |
|---|---|---|---|---|---|---|---|---|
| 101 | Me | OH | D | H | 111 | | D | H |
| 102 | Me | OH | D | D | 112 | | D | D |

TABLE 6-continued

| Example | $R_{2a}$ | $R_{2b}$ | $R_{b5}$ | $R_{b6}$ | Example | $R_{2a}$ and $R_{2b}$ | $R_{b5}$ | $R_{b6}$ |
|---|---|---|---|---|---|---|---|---|
| 103 | Me | OH | $CD_3$ | H | 113 | 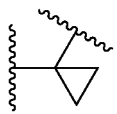 | $CD_3$ | H |
| 104 | Me | OH | $CD_3$ | D | 114 | 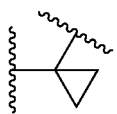 | $CD_3$ | D |
| 105 | Me | OH | H | H | 115 | 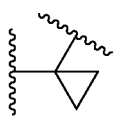 [SMILES: *C1(*)CC1] | H | H |
| 106 | Me | F | D | H | 116 | 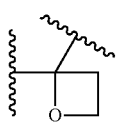 | D | H |
| 107 | Me | F | D | D | 117 | 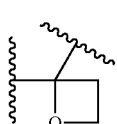 | D | D |
| 108 | Me | F | $CD_3$ | H | 118 | 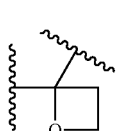 | $CD_3$ | H |
| 109 | Me | F | $CD_3$ | D | 119 | 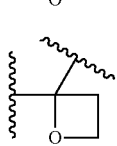 | $CD_3$ | D |
| 110 | Me | F | H | H | 120 | 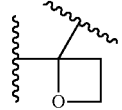 [SMILES: *C1(*)CCO1] | H | H | or a pharmaceutically acceptable salt thereof.

5. A pharmaceutical composition comprising a compound according to claim 1, or a pharmaceutically acceptable salt or ester thereof, in combination with a pharmaceutically acceptable carrier or excipient.

6. A method of treating hepatitis C in a subject in need thereof, comprising administering to the subject therapeutically effective amount of the pharmaceutical composition according to claim 5.

7. The method of claim 6, further comprising administering concurrently an additional anti-hepatitis C virus agent.

8. The method of claim 7, wherein said additional anti-hepatitis C virus agent is selected from the group consisting of α-interferon, β-interferon, ribavarin, and adamantine.

9. The method of claim 7, wherein said additional anti-hepatitis C virus agent is an inhibitor of hepatitis C virus helicase, polymerase, metalloprotease, or IRES.

10. The pharmaceutical composition of claim 5, further comprising another anti-HCV agent.

11. The pharmaceutical composition of claim 5, further comprising an agent selected from interferon, ribavirin, amantadine, another HCV protease inhibitor, an HCV polymerase inhibitor, an HCV helicase inhibitor, or an internal ribosome entry site inhibitor.

12. The pharmaceutical composition of claim 5, further comprising pegylated interferon.

\* \* \* \* \*

UNITED STATES PATENT AND TRADEMARK OFFICE
CERTIFICATE OF CORRECTION

| | | |
|---|---|---|
| PATENT NO. | : 9,718,851 B2 | |
| APPLICATION NO. | : 14/933752 | |
| DATED | : August 1, 2017 | |
| INVENTOR(S) | : Jay R. Luly et al. | |

It is certified that error appears in the above-identified patent and that said Letters Patent is hereby corrected as shown below:

On the Title Page

Under Inventors (72), after Bin Wang, delete "Brigton" and insert -- Brighton --.

In the Claims

<u>At Column 63:</u>
In Claim 3, Line 66, delete "$R_{io}$" and insert -- $R_{10}$ --.

Signed and Sealed this
Third Day of October, 2017

Joseph Matal
*Performing the Functions and Duties of the
Under Secretary of Commerce for Intellectual Property and
Director of the United States Patent and Trademark Office*